(12) United States Patent
Ohmori et al.

(10) Patent No.: US 8,232,321 B2
(45) Date of Patent: Jul. 31, 2012

(54) ALKYLENE OXIDE DERIVATIVE AND SKIN EXTERNAL PREPARATION CONTAINING THE SAME

(75) Inventors: Takashi Ohmori, Yokohama (JP); Akira Ishikubo, Yokohama (JP); Yuki Sugiyama, Yokohama (JP); Yuko Matsui, Yokohama (JP); Tomoyuki Kawasoe, Yokohama (JP); Yoji Tezuka, Kawasaki (JP); Hiroyasu Mizuno, Kawasaki (JP); Kei-ichi Maruyama, Kawasaki (JP)

(73) Assignees: Shiseido Company, Ltd., Chuo-ku, Tokyo (JP); NOF Corporation, Shibuya-ku, Tokyo (JP)

( * ) Notice: Subject to any disclaimer, the term of this patent is extended or adjusted under 35 U.S.C. 154(b) by 409 days.

(21) Appl. No.: 12/670,181

(22) PCT Filed: Jul. 25, 2008

(86) PCT No.: PCT/JP2008/063392
§ 371 (c)(1),
(2), (4) Date: Feb. 4, 2010

(87) PCT Pub. No.: WO2009/014211
PCT Pub. Date: Jan. 29, 2009

(65) Prior Publication Data
US 2010/0190864 A1    Jul. 29, 2010

(30) Foreign Application Priority Data
Jul. 26, 2007  (JP) ................. 2007-194493

(51) Int. Cl.
C08G 65/28    (2006.01)
A61K 31/77    (2006.01)
A61K 8/86     (2006.01)
A61Q 1/02     (2006.01)
A61Q 19/00    (2006.01)
A61P 17/16    (2006.01)

(52) U.S. Cl. .................... 514/723; 568/616; 424/401
(58) Field of Classification Search .................... None
See application file for complete search history.

(56) References Cited

U.S. PATENT DOCUMENTS 5,554,315 A   9/1996  Tonomura et al.
7,625,574 B2  12/2009 Ohmori et al.

FOREIGN PATENT DOCUMENTS

| JP | 7-197083 | 8/1995 |
| JP | 7-277943 | 10/1995 |
| JP | 9-100225 | 4/1997 |
| JP | 2000-136226 | 5/2000 |
| JP | 2001-302443 | 10/2001 |
| JP | 2004-83541 | 3/2004 |
| JP | 2005-47871 | 2/2005 |
| JP | 2007-45776 | 2/2007 |
| JP | 2007-91697 | 4/2007 |
| JP | 2008-115091 | 5/2008 |

OTHER PUBLICATIONS

Japanese Patent Abstract for Publication No. 2000-136226 published May 16, 2000, seven pages.
Japanese Patent Abstract for Publication No. 2001-302443 published Oct. 31, 2001, seven pages.
Japanese Patent Abstract for Publication No. 2005-047871 published Feb. 24, 2005, twenty pages.
Japanese Patent Abstract for Publication No. 2007-045776 published Feb. 22, 2007, seventy pages.
Japanese Patent Abstract for Publication No. 2007-091697 published Apr. 12, 2007, nine pages.
Japanese Patent Abstract for Publication No. 2008-115091 published May 22, 2008, 38 pages.
Japanese Patent Abstract for Publication No. 07-277943 published Oct. 24, 1995, six pages.
Japanese Patent Abstract for Publication No. 09-100225 published Apr. 15, 1997, ten pages.
International Preliminary Report on Patentability for corresponding PCT/JP2008/063392 mailed Feb. 18, 2010, five pages.
International Search Report for corresponding PCT/JP2008/063392 mailed Oct. 7, 2008, three pages.

*Primary Examiner* — Rosalynd Keys
(74) *Attorney, Agent, or Firm* — Rankin, Hill & Clark LLP

(57) ABSTRACT

The present invention is to provide a new compound having a rough skin improving effect, excellent in safety, excellent in texture in use, especially free of sticky feeling, excellent in refreshing feeling, and capable to improve the base agent stability as a component. An alkylene oxide derivative is characterized by being represented by the below-described general formula (I):

(formula I)

$$Z-\{O-[(AO)_a-(EO)_b]-R\}_2 \qquad (I)$$

(In the formula, Z is the residue obtained by removing hydroxyl groups from the dimer diol, EO is an oxyethylene group, AO is an oxyalkylene group having 3 to 4 carbon atoms, and the addition form is block-type. The symbols a and b are the average addition mole numbers of the above-described oxyalkylene group and the oxyethylene group, respectively, and they are $1 \leq a \leq 150$ and $1 \leq b \leq 150$. The percentage of the oxyethylene groups with respect to the sum of the oxyalkylene groups having 3 to 4 carbon atoms and the oxyethylene groups is 10 to 99 mass %. Rs may be either identical to or different from each other, and they are hydrocarbon groups having 1 to 4 carbon atoms.)

14 Claims, No Drawings

ALKYLENE OXIDE DERIVATIVE AND SKIN EXTERNAL PREPARATION CONTAINING THE SAME

RELATED APPLICATIONS

This application claims the priority of Japanese Patent Application No. 2007-194493 filed on Jul. 26, 2007, which are incorporated herein by reference.

TECHNICAL FIELD

The present invention relates to new alkylene oxide derivatives, and in particular, relates to the alkylene oxide derivatives that have a rough skin improving effect, are safe and excellent in texture in use, and are a component that can improve the stability of a base agent.

BACKGROUND ART

There are various forms of skin external preparations such as lotion, milky lotion, and cream. Among them, the lotion is one of the essential items for basic cosmetics. In order to stably blend water-insoluble materials such as perfume, oil components, and oil-soluble agents as well as water and water-soluble material such as a moisturizing component into a lotion, various base-stabilizing technologies (solubilization technologies) with the use of a surfactant have been proposed (for example, refer to patent literatures 1 and 2).

The stability of a base agent can be improved by the suitable selection of a conventional surfactant or by blending a substantial amount thereof. However, it is one of the causes of rough skin, and the improvement of texture in use has not been satisfactory. In recent years, the higher safety of skin external preparations is expected. From this standpoint, the presence of a surfactant was sometimes regarded as a problem. Although the surfactant is an essential component in numerous skin external preparations from the standpoint of the improvement of base agent stability, it is the main cause of rough skin and poor texture in use. Thus, there has been a problem to be solved in that the commercial value of the product is lost on a big scale.

Therefore, from the standpoint that the water-retaining function should be supplied to the skin, the moisturizers such as polyol compounds such as glycerin, sorbitol, and propylene glycol; and mucopolysaccharides such as hyaluronic acid; amino acids as NMF (natural moisturizing factor); agents such as tranexamic acid; and various extracts have usually been blended in skin external preparations as an active component having improving and preventing effects of rough skin. In addition, the method to make up for the stratum corneum barrier function with an occluding agent such as petrolatum ointment and the method to activate skin cells with vitamins, hormones, etc. have been used (for example, refer to patent literatures 3 and 4).

However, in order to enhance a moisturizing effect and a rough skin improving effect, the blending quantity needs to be increased in the case of glycerin or other moisturizers. As a result, the following problems that should be solved are generated. The base agent stability deteriorates and the usability becomes poor. When applied on the skin, it is repelled by sebum and the compatibility with the skin becomes poor. A polysaccharide precipitates in the formulations containing a large amount of alcohol. In the case of amino acids such as DL-threonine, there are drawbacks such as color generation and malodor. The agent such as tranexamic acid has a problem in long-term stability. When an occlusion agent such as petrolatum is used, there is a drawback in that an unpleasant texture such as an oily and sticky feeling is generated. Furthermore, when extracts, vitamins, hormones, and the like are used, there are to-be-solved problems such as safety issues related to side effects and long-term stability.

Thus, the development of a component that has a rough skin improving effect, excellent safety, and excellent texture in use and that can improve base agent stability has been awaited.

Patent literature 1: Japanese Unexamined Patent Publication No. 2001-302443
Patent literature 2: Japanese Unexamined Patent Publication No. 2005-47871
Patent literature 3: Japanese Unexamined Patent Publication No. H9-100225
Patent literature 4: Japanese Unexamined Patent Publication No. H7-277943

DISCLOSURE OF THE INVENTION

Problem to be Solved by the Invention

The present invention was made in view of the above-described problems, and an object of the invention is to provide a new compound having a rough skin improving effect, excellent in safety, excellent in texture in use, especially free of sticky feeling, excellent in refreshing feeling, and capable to improve the base agent stability as a component of the skin external preparation.

Means to Solve the Problem

In order to achieve the above-described object, the present inventors have conducted a study. As a result, the present inventors have found that a block-type alkylene oxide/ethylene oxide-dimer diol ether with a specific structure has a rough skin improving effect, excellent safety, excellent texture in use, especially no sticky feeling, and an excellent refreshing feeling, and have also found that when blended in a skin external preparation, it functions as a surfactant, and the excellent base agent stability can be achieved, thus leading to completion of the present invention.

That is, the alkylene oxide derivative of the present invention is characterized by being represented by the below-described general formula (I).

$$Z-\{O-[(AO)_a-(EO)_b]-R\}_2 \qquad (I)$$

(In the formula, Z is the residue obtained by removing hydroxyl groups from the dimer diol, EO is an oxyethylene group, AO is an oxyalkylene group having 3 to 4 carbon atoms, and the addition form is block-type. The symbols a and b are the average addition mole numbers of the above-described oxyalkylene group and the oxyethylene group, respectively, and they are $1 \leq a \leq 150$ and $1 \leq b \leq 150$. The percentage of the oxyethylene groups with respect to the sum of the oxyalkylene groups having 3 to 4 carbon atoms and the oxyethylene groups is 10 to 99 mass %. Rs may be either identical to or different from each other, and they are hydrocarbon groups having 1 to 4 carbon atoms.)

In the above-described alkylene oxide derivative, it is preferable that AO shown in the general formula (I) is an oxybutylene group.

In the above-described alkylene oxide derivative, it is preferable that Z shown in the general formula (I) is a dimer diol residue having 24 to 48 carbon atoms.

In addition, the skin external preparation of the present invention is characterized by comprising the above-described alkylene oxide derivative.

In the above-described skin external preparation, it is preferable that the content of the above-described alkylene oxide derivative is 0.01 to 70 mass %.

In addition, the rough skin improving agent of the present invention is characterized by comprising the above-described alkylene oxide derivative as the active component.

In addition, the usability-improving agent for cosmetics of the present invention is characterized by comprising the above-described alkylene oxide derivative as the active component.

Effect of the Invention

The alkylene oxide derivative with a specific structure of the present invention has a rough skin improving effect, excellent safety, excellent texture in use, especially no sticky feeling, and an excellent refreshing feeling. In addition, when blended in a skin external preparation, it functions as a surfactant and can improve the base agent stability.

BEST MODE FOR CARRYING OUT THE INVENTION

In the following, a preferable embodiment of the present invention will be described.

The alkylene oxide derivative of the present invention is characterized by being represented by the below-described general formula (I).

In the alkylene oxide derivative represented by the formula (I), Z is the residue obtained by removing hydroxyl groups from the dimer diol, EO is an oxyethylene group. AO is an oxyalkylene group having 3 to 4 carbon atoms, and the examples include an oxypropylene group, an oxybutylene group, an oxyisobutylene group, an oxy-t-butylene group. AO is preferably an oxypropylene group or an oxybutylene group, and more preferably an oxybutylene group. The addition form of these is block-type.

The symbols a and b are the average addition mole numbers of the above-described oxyalkylene group and the oxyethylene group, respectively, and they are $1 \leq 2a \leq 150$ and $1 \leq 2b \leq 150$. They are preferably $2 \leq 2a \leq 70$ and $5 \leq 2b \leq 120$, and more preferably $2 \leq 2a \leq 50$ and $10 \leq 2b \leq 100$. If 2 a is zero, the texture in use tends to be poor. If 2 a exceeds 150, the moisturizing effect feeling tends to be poor. If 2 b is zero, the moisturizing effect and the rough skin improving effect tend to be poor, and it does not function as a surfactant. If 2 b exceeds 150, the sticky feeling tends to be generated.

The percentage of EO with respect to the sum of AO and EO in the above-described formula (I) is 10 to 99 mass % and preferably 20 to 70 mass %. If the percentage is smaller than 10 mass %, the moisturizing effect feeling tends to be poor.

In addition, the addition form of oxyethylene groups and oxyalkylene groups having 3 to 4 carbon atoms is block-type. If the addition form is random-type, it will not function as a surfactant, and the base agent stability will be poor. The addition order with respect to the dimer diol is preferably in the bonding order of AO and EO.

R is a hydrocarbon group having 1 to 4 carbon atoms. By the alkyl etherification of the terminal hydroxyl group, which is the cause of stickiness, the skin compatibility is improved and a good feeling in use is generated. Examples of hydrocarbon groups include a methyl group, ethyl group, n-propyl group, isopropyl group, n-butyl group, sec-butyl group, tert-butyl group, and mixed groups thereof. In the present invention, a methyl group and ethyl group are preferable. If the number of carbon atoms is larger than 5, the moisturizing effect feeling tends to be poor.

In the alkylene oxide derivative represented by formula (I), Z is the residue obtained by removing hydroxyl groups from a dimer diol. The dimer diol is a diol obtained by reducing a dimer acid. The dimer diol residue is essential to provide a refreshing feeling and base agent stability.

The dimer acid that is a raw material of the dimer diol used in the present invention is a dimer obtained by polymerizing, for example, an unsaturated fatty acid or its lower alcohol ester. Specifically, the dimer acid can be synthesized by reacting unsaturated fatty acids such as oleic acid, linoleic acid, and linolenic acid or their ester of a lower alcohol by thermal polymerization like the Diels-Alder reaction or other reaction methods. In the formed dimer acid, an unreacted fatty acid may remain so far as the effect of the present invention is not undermined.

The dimer acid obtained by dimerizing an unsaturated fatty acid having 12 to 24 carbon atoms or its ester of a lower alcohol is preferable. In this case, Z is the dimer diol residue having 24 to 48 carbon atoms. Examples of such unsaturated fatty acids include myristoleic acid, palmitoleic acid, oleic acid, elaidic acid, vaccenic acid, gadoleic acid, erucic acid, nervonic acid, linoleic acid, linolenic acid, and their esters of a lower alcohol having 1 to 3 carbon atoms. An unsaturated fatty acid having 18 carbon atoms is preferable, and oleic acid, linoleic acid, or its lower alcohol ester is especially preferable. A dimer acid wherein the remaining unsaturated double bond is hydrogenated, after dimerization, can be also used.

As dimer diols, animal fat derived and vegetable fat derived dimer diols are distributed. Although either can be used in the present invention, vegetable fat derived dimer diols are preferable. Examples of such dimer diols include Sovermol 908 manufactured by Cognis Japan Ltd., Pripol 2033 manufactured by Uniqema, and Pespol HP-1000 manufactured by Toagosei Co., Ltd.

Specific examples of alkylene oxide derivatives of the present invention include, POB(25)POE(34)dimethyl dimer diol ether, POB(25)POE(35) dimethyl dimer diol ether, POB (4)POE(13) dimethyl dimer diol ether, POB(25)POE(52) dimethyl dimer diol ether, POB(18)POE(41) dimethyl dimer diol ether, POB(18)POE(41) diethyl dimer diol ether, POB (18)POE(41) dipropyl dimer diol ether, POB(18)POE(41) dibutyl dimer diol ether, POB(11)POE(30) dimethyl dimer diol ether, POB(15)POE(45) dimethyl dimer diol ether, POB (18)POE(50) dimethyl dimer diol ether, POB(21)POE(56) dimethyl dimer diol ether, POB(12)POE(50) dimethyl dimer diol ether, POB(18)POE(61) dimethyl dimer diol ether, POB (3)POE(40) dimethyl dimer diol ether, POB(6)POE(82) dimethyl dimer diol ether, POB(40)POE(120) dimethyl dimer diol ether, POB(100)POE(40) dimethyl dimer diol ether, POE(35)POP(30) dimethyl dimer diol ether, POE(52)POP (30) dimethyl dimer diol ether.

The above-described POE, POP, and POB are the abbreviations of polyoxyethylene, polyoxypropylene, and polyoxybutylene, respectively. Hereinafter, they may be abbreviated as such. The addition mole numbers of the above-described respective POE, POP, and POB are the total addition mole numbers in the molecule, namely, they are described as the values 2 a and 2 b.

Alkylene oxide derivatives represented by formula (I) can be produced by a publicly known method. For example, they can be obtained by the addition polymerization of an alkylene oxide having 3 to 4 carbon atoms and ethylene oxide, in that order, to a dimer diol and by performing an ether reaction with an alkyl halide in the presence of an alkaline catalyst.

By blending an alkylene oxide derivative represented by the above-described formula (I) into a skin external preparation, the rough skin improving effect can be achieved. In addition, the texture in use such as an absence of sticky feeling and a refreshing feeling can be improved. Furthermore, the base agent stability can be improved by its functioning as a surfactant.

Thus, the alkylene oxide derivative of the present invention represented by formula (I) can be suitably used for skin external preparation. In addition, it can be used independently as a rough skin improving agent or a usability-improving agent of cosmetics.

In the skin external preparation of the present invention, the blending quantity of the above-described alkylene oxide derivative is normally 0.01 to 70 mass % of the total composition and preferably 0.1 to 20 mass %. If the blending quantity is less than 0.01 mass %, the manifestation of the blending effect may not be satisfactory. If the blending quantity exceeds 70 mass %, a sticky feeling may be generated after use.

In the skin external preparation of the present invention, in addition to the above-described alkylene oxide derivative, the components normally used in cosmetics or quasi-drug skin external preparations can be blended, and they are produced according to conventional methods. In the following, specific blendable components are listed. The skin external preparation of the present invention can be prepared by blending the above-described alkylene oxide derivative and one or more of the below-described components.

Examples of moisturizers include polyethylene glycol, propylene glycol, glycerin, 1,3-butylene glycol, xylitol, sorbitol, maltitol, chondroitin sulfate, hyaluronic acid, mucoitin sulfate, charonic acid, atelocollagen, cholesteryl 12-hydroxystearate, sodium lactate, bile salts, dl-pyrrolidone carboxylates, short-chain soluble collagen, diglycerin (EO)PO adduct, chestnut rose extract, yarrow extract, and melilot extract.

Examples of powder components include inorganic powder (for example, talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstate, magnesium, silica, zeolite, barium sulfate, calcined calcium sulfate, calcium phosphate, fluorine apatite, hydroxyapatite, ceramic powder, metallic soap (for example, zinc myristate, calcium palimitate, and aluminum stearate), and boron nitride); organic powder (for example, polyamide resin powder (nylon powder), polyethylene powder, polymethylmethacrylate powder, polystyrene powder, styrene-acrylic acid copolymer resin powder, benzoguanamine resin powder, poly(tetrafluoroethylene) powder, and cellulose powder); inorganic white family pigment (for example, zinc oxide); inorganic red family pigment (for example, iron titanate); inorganic purple family pigment (for example, mango violet, cobalt violet); inorganic green family pigment (for example, chrome oxide, chrome hydroxide, cobalt titanate); inorganic blue family pigment (for example, ultramarine, iron blue); pearl pigment (for example, titanium oxide coated mica, titanium oxide coated bismuth oxychloride, titanium oxide coated talc, colored titanium oxide coated mica, bismuth oxychloride, argentine); metal powder pigment (for example, aluminum powder, and copper powder); organic pigment such as zirconium, barium, or aluminum lake (for example, organic pigment such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, Blue No. 404, or Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); natural pigment (for example, chlorophyll, and β-carotene).

Examples of liquid fats include avocado oil, camellia oil, turtle oil, *macadamia* nut oil, corn oil, mink oil, olive oil, rapeseed oil, egg yolk oil, sesame oil, par chic oil, wheat germ oil, sasanqua oil, castor oil, linseed oil, safflower oil, cotton seed oil, *perilla* oil, soybean oil, groundnut oil, brown real oil, torreya oil, rice bran oil, chinese wood oil, jojoba oil, germ oil, and triglycerol.

Examples of solid fats include cacao butter, coconut oil, horse fat, hydrogenated coconut oil, palm oil, beef fat, mutton suet, hydrogenated beef fat, palm kernel oil, lard, beef bones fat, Japan wax kernel oil, hardened oil, hoof oil, Japan wax, and hydrogenated caster oil.

Examples of waxes include beeswax, candelilla wax, cotton wax, carnauba wax, bayberry wax, insect wax, spermaceti, montan wax, bran wax, lanolin, kapok wax, lanolin acetate, liquid lanolin, sugarcane wax, lanolin fatty acid isopropyl, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol, and POE hydrogenated lanolin alcohol ether.

Examples of hydrocarbon oils include liquid paraffin, ozocerite, squalene, pristane, paraffin, ceresin, squalane, vaseline, and microcrystalline wax.

Examples of higher fatty acids include lauric acid, myristic acid, palmitic acid, stearic acid, behenic acid, oleic acid, undecylenic acid, tallic acid, isostearic acid, linoleic acid, linolenic acid, eicosapentaenoic acid(EPA), and docosahexaenoic acid(DHA).

Examples of higher alcohols include linear alcohol (for example, lauryl alcohol, cetyl alcohol, stearyl alcohol, behenyl alcohol, myristyl alcohol, oleyl alcohol, and cetostearyl alcohols); branched-chain alcohols (for example, monostearylglycerin ether (batyl alcohol), 2-decyltetradecinol, lanolin alcohol, cholesterol, phytosterol, hexyldodecanol, isostearyl alcohol, and octyldodecanol).

Examples of synthetic ester oils include isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxy stearate, ethylene glycol di-2-ethyl hexanoate, di-penta erythritol fatty acid ester, N-alkyl glycol monoisostearate, neopentyl glycol dicaprate, diisostearyl malate, glycerol di-2-heptyl undecanoate, trimethyrol propane tri-2-ethyl hexanoate, trimethyrol propane triisostearate, tetra-2-ethyl hexanoate pentaerythritol, glycerol tri-2-ethyl hexanoate, glycerol trioctanoate, glycerol triisopalmitate, trimethyrol propane triisostearate, cetyl 2-ethylhexanoate, 2-ethylhexyl palmitate, glycerol trimyristate, glyceride tri-2-heptyl undecanoate, castor oil fatty acid methyl ester, oleyl oleate, acetoglyceride, 2-heptylundecyl palmitate, diisobutyl adipate, N-lauroyl-L-glutamic acid-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, and triethyl citrate.

Examples of silicone oils include chain polysiloxane (for example, dimethylpolysiloxane, methylphenylpolysiloxane, and diphenylpolysiloxane); cyclic polysiloxane (for example, octamethylcyclotetrasiloxane, decamethylcyclopentasiloxane, and dodecamethylcyclohexasiloxane), silicone resins having a three dimensional network structure, silicone rubber, various modified polysiloxanes (for example, amino-modified polysiloxane, polyether-modified polysiloxane, alkyl-modified polysiloxane, and fluorine-modified polysiloxane), and acrylic silicone.

Examples of anionic surfactants include fatty acid soap (for example, sodium laurate, and sodium palmitate); higher alkyl sulfate ester salt (for example, sodium lauryl sulfate, and potassium lauryl sulfate); alkyl ether sulfate ester salt (for example, POE-lauryl sulfate triethanolamine, and sodium POE-lauryl sulfate); N-acyl sarcosinic acid (for example, sodium lauroyl sarcocinate); higher fatty acid amide sulfonate (for example, sodium N-myristoyl-N-methyl taurine, sodium coconut oil fatty acid methyl tauride, and sodium laurylmethyl tauride); phosphate ester salt (sodium POE-oleylether phosphate, and POE-stearylether phosphate); sulfosuccinate (for example, sodium di-2-ethylhexyl sulfosuccinate, sodium monolauroyl monoethanolamide polyethylene sulfosuccinate, and sodium lauryl polypropylene glycol sulfosuccinate); alkylbenzene sulfonate (for example, sodium linear dodecylbenzene sulfonate, triethanolamine linear dodeylbenzene sulfonate, and linear dodecylbenzene sulfonate); higher fatty acid ester sulfate ester salt (for example, sodium hydrogenated gryceryl cocoate sulfate); N-acyl glutamate (for example, monosodium N-lauroyl glutamate, disodium N-stearoyl glutamate, and monosodium N-myristoyl-L-glutamate); sulfonated oil (for example, Turkey red oil); POE-alkyl ether carboxylic acid; POE-alkyl aryl ether carboxylate; α-olefine sulfonate; higher fatty acid ester sulfonate; secondary alcohol sulfate ester salt; higher fatty acid alkylolamide sulfate ester salt; sodium lauroyl monoethanolamide succinate; N-palmitoyl asparaginate ditriethanolamine; and sodium casein.

Examples of cationic surfactants include alkyltrimethyl ammonium salt (for example, stearyltrimethyl ammonium chloride, and lauryltrimethyl ammonium chloride); alkylpyridinium salt (for example, cetylpyridinium chloride); distearyldimethyl ammonium chloride; dialkyldimethyl ammonium salt; poly (N,N'-dimethyl-3,5-methylenepiperidinium) chloride; alkyl quaternary ammonium salt; alkyldimethylbenzyl ammonium salt; alkylisoquinolinium salt; dialkylmorphonium salt; POE-alkylamine; alkylamine salt; polyamine fatty acid derivative; amyl alcohol fatty acid derivative; benzalkonium chloride; and benzethonium chloride.

Examples of ampholytic surfactants include imidazoline base ampholytic surfactant (for example, sodium 2-undecyl-N,N,N-(hydroxyethylcarboxymethyl)-2-imidazoline, 2-cocoyl-2-imidazolinium hydroxide-1-carboxyethyloxy)-2-sodium salt; and betaine base surfactant (for example, 2-heptadecyl-N-carboxymethyl-N-hydroxyethylimidazolinium betaine, lauryldimethyl aminoacetate betaine, alkyl betaine, amidobetaine, and sulfobetaine).

Examples of lipophilic nonionic surfactants include sorbitan fatty acid esters (for example, sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2 ethylhexylate, and diglycerol sorbitan tetra-2 ethylhexylate); glyceryl polyglyceryl fatty acids (for example, glyceryl monocotton oil fatty acid, glyceryl monoerucate, glyceryl sesquioleate, glyceryl monostearate, glyceryl α,α'-oleate pyroglutamate, and glyceryl monostearate malate); propylene glycol fatty acid esters (for example, propylene glycol monostearate); hydrogenated caster oil derivative; and glyceryl alkyl ether.

Examples of hydrophilic nonionic surfactants include POE-sorbitan fatty acid esters (for example, POE-sorbitan monooleate, POE-sorbitan monostearate, and POE-sorbitan tetraoleate); POE-sorbit fatty acid esters (for example, POE-sorbit monolaurate, POE-sorbit monooleate, POE-sorbit pentaoleate, and POE-sorbit monostearate), POE-glyceryl fatty acid esters (for example, POE-glyceryl monostearate; POE-glyceryl monoisostearate, and POE-glyceryl triisostearate); POE-fatty acid esters (for example, POE-distearate, POE-monodioleate, and ethyleneglycol distearate); POE-alkyl ethers (for example, POE-lauryl ether, POE-oleyl ether, POE-stearyl ether, POE-behenyl ether, POE-2-octyldodecyl ether, and POE-cholestanol ether); pluronic types (for example, Pluronic), POE/POP-alkyl ethers (for example, POE/POP-cetyl ether, POE/POP-2-decyltetradecyl ether, POE/POP-monobutyl ether, POE/POP-hydrogenated lanoline, and POE/POP glycerin ether); tetra POE/tetra POP-ethylenediamine condensation products (for example, Tetronic); POE-castor oil hydrogenated castor oil derivatives (for example, POE-caster oil, POE-hydrogenated caster oil, POE-hydrogenated caster oil monoisostearate, POE-hydrogenated castor oil triisostearate, POE-hydrogenated caster oil monopyroglutamate monoisostearate diester, and POE-hydrogenated oil maleate); POE-beeswax/lanoline derivatives (for example, POE-sorbitol beeswax); alkanolamides (for example, coconut oil fatty acid diethanolamide, lauric acid monoethanolamide, and fatty acid isopropanolamide); POE-propyleneglycol fatty acid esters; POE-alkyl amines; POE-fatty acid amides; sucrose fatty acid esters; alkylethoxydimethylamine oxide; and trioleyl phosphoric acid.

Examples of natural water-soluble polymers include plant-based polymer (for example, gum Arabic, gum tragacanth, galactan, guar gum, locust bean gum, gum karaya, carrageenan, pectine, agar, quince seed (*cyclonia oblonga*), algae colloid (brown algae extract), starch (rice, corn, potato, and wheat), and glicyrrhizic acid), microorganisms based polymer (for example, xanthan gum, dextran, succinoglycan, and pullulan), animal-based polymer (for example, collagen, casein, and albumin, gelatine).

Examples of semisynthetic water-soluble polymers include starch-based polymer (for example, carboxymethyl starch, and methylhydroxypropyl starch), cellulosic polymer (methylcellulose, ethylcellulose, methylhydroxypropylcellulose, hydroxyethylcellulose, cellulose sodium sulfate, hydroxypropylcellulose, carboxymethylcellulose, sodium calboxymethyl cellulose, micrclrystalline cellulose, and cellulose powder), and algin acid base polymer (for example, sodium alginate, and propylene glycol ester alginate).

Examples of synthetic water-soluble polymers include vinyl base polymer (for example, polyvinyl alcohol, polyvinyl methyl ether, polyvinylpyrrolidone, and carboxyvinylpolymer); polyoxyethylene base polymer (for example, polyethylene glycol 20,000, 40,000, and 60,000); acrylic polymer (for example, sodium polyacrylate, polyethylacrylate, and polyacrylamide); polyethyleneimine; and cation-polymer.

Examples of plasticizers include, for example, gum Arabic, carrageenan, gum karaya, gum tragacanth, locust bean gum, quince seed (*cyclonia oblonga*), casein, dextrine, gelatine, sodium pectate, sodium alginate, methylcellulose, ethylcellulose, CMC, hydroxyethylcellulose, hydroxypropylcellulose, PVA, PVM, PVP, sodium polyacrylate, carboxyvinylpolymer, locust bean gum, guar gum, tamarind gum, dialkyldimethylammonium cellulose sulfate, xanthan gum, aluminium magnesium silicate, bentonite, hectorite, aluminium magnesium silicate (veegum), laponite, and silicic anhydride.

Examples of ultraviolet light absorbers include benzoic acid family ultraviolet light absorbers (for example, p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester; N,N-dimethyl PABA butyl ester, and N,N-dimethyl PABA ethyl ester); anthranilic acid family ultraviolet light absorbers (for example, homomethyl N-acetylanthranilate); salicylic acid family ultraviolet light absorbers (for example, amyl salicylate, menthyl salicylate, homomethyl salicylate, octyl salicylate, phenyl salicylate, benzyl salicylate, and p-isopropanolphenyl salicylate); cinnamic acid family ultraviolet light absorbers (for example, octyl cinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, and glyceryl mono-2-ethylhexanoyl-diparamethoxy cinnamate); benzophenone family ultraviolet light absorbers (for example, 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,l-camphor, 3-benzylidene-d,l-camphor; 2-phenyl-5-methylbenzoxazol; 2,2'-hydroxy-5-methylphenylbenzotriazol; 2-(2'-hydroxy-5'-t-octylphenyl)benzotriazol, 2-(2'-hydroxy-5'-methylphenylbenzotriazol; dibenzalazine; dianisoylmethane; 4-methoxy-4'-t-butyldibenzoylmethane; and 5-(3,3-dimethyl-2-norbornylidene)-3-pentane-2-one.

Examples of lower alcohols include ethanol, propanol, isopropanol, isobutyl alcohol, t-butyl alcohol.

Examples of polyhydric alcohols include dihydric alcohol (for example, ethylene glycol, propylen glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol); trihydric alcohol (for example, glycerin, and trimethylolpropane); tetrahydric alcohol (for example, pentaerythritol such as 1,2, 6-hexanetriol); pentahydric alcohol (for example, xylitol); hexahydric alcohol (for example, sorbitol, and mannitol); polyhydric alcohol polymer (for example, diethylene glycol, triethylene glycol, polypropylene glycol, tetraethylene glycol, diglycerin, polyethylene glycol, triglycerin, tetraglycerin, and polyglycerin); dihydric alcohol alkyl ethers (for example, ethylene glycol monomethyl ether, ethylene glycol monoethyl ether, ethylene glycol monobutyl ether, ethylene glycol monophenyl ether, ethylene glycol monohexyl ether, ethylene glycol mono2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether); dihydric alcohol alkyl ethers (for example, diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether ethers (for example, ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disaccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin monoalkyl ether (for example, chimil alcohol, selachyl alcohol, and batyl alcohol); sugar alcohol (for example, sorbitol, maltitol, maltotriose, mannitol, sucrose, erythritol, glucose, fructose, starch sugar, maltose, xylitose, and starch sugar hydrogenated alcohol); glysolid; tetrahydrofurfuryl alcohol; POE-tetrahydrofurfuryl alcohol; POP-butyl ether; POP/POE-butyl ether; tripolyoxypropylene glycerin ether; POP-glycerin ether; POP-glycerin ether phosphoric acid; POP/POE-pentaerythritol ether; and polyglycerin.

Examples of monosaccharides include triose (for example, D-glyceryl aldehyde, and dihydroxyacetone); tetrose (for example, D-erythrose, D erythrulose, D-threose, and erythritol); pentaose (for example, L-arabinose, D-xylose, L-lyxose, D-arabinose, D-ribose, D-ribulose, D-xylulose, and L-xylulose); hexylose (for example, D-glucose, D-talose, D-psicose, D-galactose, D-fructose, L-galactose, L-mannose, and D-tagatose); heptose (for example, aldoheptose, and heplose); octose (for example, octulose); deoxy sugar (for example, 2-deoxy-D-ribose, 6-deoxy-L galactose, and 6-deoxy-L-mannose); amino sugar (for example, D-glucosamine, D-galactosamine, sialic acid, amino uronic acid, and muramic acid); and uronic acid (for example, D-grucuronic acid, D-mannuronic acid, L-guluronic acid, D-garacturonic acid, and L-iduronic acid).

Examples of oligosaccharides include sucrose, guntianose, umbelliferose, lactose, planteose, isolignoses, α,α-trehalose, raffinose, lignoses, umbellicine, stachyose, and verbascoses.

Examples of amino acids include neutral amino acid (for example threonine, and cysteine); and basic amino acid (for example, hydroxylysine). Examples of amino acid derivatives include sodium acyl sarcosine (sodium lauroyl sarcosine), acyl glutamate, sodium acyl β-alanine, glutathione, and pyrrolidone carboxylate.

Examples of the organic amines include monoethanolamine, diethanolamine, triethanolamine, morpholine, triisopropanolamine, 2-amino-2-methyl-1,3-propanediol, and 2-amino-2-methyl-1-propanol.

Examples of chelate agents include 1-hydroxyethane-1,1-diphosphonic acid, 1-hydroxyethane-1,1-diphosphonic acid 4Na salt, disodium edetate, trisodium edetate, tetrasorium edetate, sodium citrate, sodium polyphosphate, sodium metaphosphate, gluconic acid, phosphoric acid, citric acid, ascorbic acid, succinic acid, edetic acid, and trisodium hydroxyethyl ethylenediamine triacetate.

Examples of anti-oxidant aids include phosphoric acid, citric acid, ascorbic acid, maleic acid, malonic acid, succinic acid, fumaric acid, cephalin, hexamethaphosphate, phytic acid, and ethylene diamine tetra-acetic acid.

Examples of other blendable components include antiseptic agent (ethylparaben, butylparaben, etc); lightening agent (for example, placental extract, saxifrage extract, and arbutin); blood circulation promotion agent (for example, nicotine acid, nicotine acid benzyl, tocopherol nicotinate, nicotine acid β-butoxy ester, minoxidil, or their analogs, vitamin E type, γ-oryzanol, alkoxycarbonylpyridine N-oxide, capronium chloride, acetylcholine and their derivatives); various extract (for example, ginger, oat, Japanese coptis, lithospermum, birch, loquat, carrot, aloe, mallow, iris, grape, sponge gourd, lily, saffron, cnidium rhizome, ginger, *hypericum*, restharrow, garlic, red pepper, citrus unshiu, Japanese angelica, Japanese tree peoney, and seaweed); activator agent (for example, pantothenyl ethyl ether, nicotinamide, biotin, pantothenic acid, royal jelly, and cholesterol derivative); and antiseborrheric agent (for example, pyridoxine, and thianthl).

The external skin preparation of the present invention can be in any form, and the examples include a solution form, solubilized form, emulsion form, dispersed powder form, water-oil double-layer form, water-oil-powder triple-layer form, lotion, gel, mist, spray, mousse, roll-on, and stick.

The alkylene oxide derivative of the present invention can be suitably used, in addition to the application to the above-described skin external preparation, for example, as skin cleanser, hair conditioning agents, and bath preparation compositions.

In recent years, the cosmetics with good skin adhesion and low makeup deterioration against moisture and sebum, etc., namely long-lasting cosmetics have been developed. Therefore, in order to improve the cosmetic-removal effect, the blending quantities of alcohol, oil component, and surfactant in cleansers were increased. However, there have been issues such as skin irritation and deterioration in texture in use. On the other hand, the development of an oily base with a good texture in use and good skin compatibility is underway. However, a skin cleanser that satisfies all the requirements in safety, texture in use, and cleansing effect, has not yet been obtained.

On the other hand, by blending a combination of 0.1 to 20 mass % of the alkylene oxide derivative of the present invention and 1 to 20 mass % of a moisturizer composed of dipropylene glycol and/or glycerin into skin cleanser, a skin cleanser having a good texture in use, especially excellent rinsability during cleansing, a light fresh feeling after cleansing, no frictional feeling, high cosmetic cleansing effect, and low skin irritation can be obtained.

In the above-described skin cleanser, the blending quantity of the alkylene oxide derivative is normally 0.1 to 20 mass % of the total skin cleanser and preferably 1 to 10 mass %. If the blending quantity is less than 0.1 mass %, the manifestation of the blending effect may not be satisfactory. If the blending quantity exceeds 20 mass %, a sticky feeling after cleansing may be generated.

In addition, in the above-described skin cleanser, the blending quantity of the moisturizer composed of dipropylene glycol and/or glycerin is 0.1 to 20 mass % and preferably 1 to 10 mass %. If the blending quantity of dipropylene glycol and/or glycerin is less than 0.1 mass %, the manifestation of the blending effect may not be satisfactory. If the blending quantity exceeds 20 mass %, a sticky feeling after use tends to be generated.

In the above-described skin cleanser, the blendable moisturizer is not limited to the above-described dipropylene glycol and glycerin, and other moisturizer components can be suitably blended. Examples of other moisturizers include polyethylene glycol, propylene glycol, 1,3-butylene glycol, xylitol, sorbitol, maltitol, chondroitin sulfate, hyaluronic acid, mucoitin sulfate, charonic acid, atelocollagen, cholesteryl 12-hydroxystearate, sodium lactate, bile salts, dl-pyrrolidone carboxylates, short-chain soluble collagen, diglycerin (EO)PO adduct, chestnut rose extract, yarrow extract, and melilot extract.

The above-described skin cleanser can be in any form, and the examples include a solution form, solubilized form, emulsion form, dispersed powder form, water-oil double-layer form, and water-oil-powder triple-layer form.

The above-described skin cleanser is suitably used for the cleansing of the skin, in particular, for the cleansing of the skin after makeup or after the application of sunscreen. It is preferable to be in a lotion form, gel form or cream form.

In the hair conditioning agents such as hair rinse, hair treatment, and hair conditioner, hair treatment agents such as a cationic surfactant and an oil component are generally blended. However, when a quaternary ammonium salt, which is widely used as a cationic surfactant, is blended in a large amount, there has been an issue in eye and skin irritation. On the other hand, hair conditioning agents with the use of an amidoamine based cationic surfactant is also reported. However, compared with the use of quaternary ammonium salt, the smooth feeling and moist feeling to the hair were poor. On the other hand, the improvement of the texture in use has been tried by blending an oil component such as a silicone compound. However, there have been issues in that a dry and brittle feeling and a sticky feeling are generated.

On the other hand, by blending a combination of an alkylene oxide derivative of the present invention, a cationic surfactant, and a protein and/or a basic amino acid derivative into a hair conditioning composition, a hair conditioning composition that provides a light rustling feeling and moist feeling to the hair and has an excellent texture in use, such as the improvement in the smooth feeling, supple feeling, and elastic feeling, can be obtained.

In the above-described hair conditioning composition, the blending quantity of the alkylene oxide derivative is preferably 0.01 to 10 mass % of the total composition and more preferably 0.1 to 5 mass %. If the blending quantity is less than 0.01 mass %, the manifestation of the blending effect may not be satisfactory. If the blending quantity exceeds 10 mass %, a sticky feeling tends to be generated after use.

In addition, the above-described hair conditioning composition contains a quaternary ammonium salt represented by the below-described formula (II) as the cationic surfactant.

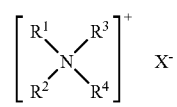
(II)

In the above-described formula (II), $R^1$ represents an alkyl group having 14 to 22 carbon atoms or a hydroxyl group, $R^2$, $R^3$ and $R^4$ independently represent an alkyl group having 1 to 3 carbon atoms, a hydroxyl group, or a benzyl group, and X represents a halogen atom or an alkyl sulfate group having 1 to 2 carbon atoms.

Examples of quaternary ammonium salts include cetyltrimethylammonium chloride, stearyltrimethylammonium chloride, behenyltrimethylammonium chloride, behenyldimethylhydroxyethylammonium chloride, stearyldimethylbenzyl ammonium chloride, and cetyltriethylammonium methylsulfate.

In addition to the above-described quaternary ammonium salt, the above-described hair conditioning composition may contain, as a cationic surfactant, an amidoamine compound represented by the below-described formula (III) or an acid addition salt thereof.

$$R^5CONH(CH_2)_nN(R^6)_2 \qquad (III)$$

In the above-described formula (III), $R^5$ represents the residue of a higher fatty acid having 13 to 23 atoms, $R^6$ represents an alkyl group having 1 to 4 carbon atoms, and n represents integers of 2 to 4.

Examples of the above-described amidoamine compounds include stearic acid diethylaminoethylamide, stearic acid dimethylaminoethylamide, palmitic acid diethylaminoethylamide, palmitic acid dimethylaminoethylamide, myristic acid diethylaminoethylamide, myristic acid dimethylaminoethylamide, behenic acid diethylaminoethylamide, behenic acid dimethylaminoethylamide, stearic acid diethylaminopropylamide, stearic acid dimethylaminopropylamide, palmitic acid diethylaminopropylamide, palmitic acid dimethylaminopropylamide, myristic acid diethylaminopropylamide, myristic acid dimethylaminopropylamide, behenic acid diethylaminopropylamide, and behenic acid dimethylaminopropylamide.

The acid addition salt of an amidoamine compound that is blended in the above-described hair conditioning composition is a compound obtained by neutralizing the above-described amidoamine compound with a normal acid, and it can easily be prepared by reacting an amidoamine compound and an acid. Examples of acids used for the production of such an acid addition salt of an amidoamine compound include low molecular weight aliphatic carboxylic acids such as acetic acid, lactic acid, citric acid, and succinic acid; inorganic acids such as hydrochloric acid, sulfuric acid, phosphoric acid, and nitric acid; and aromatic carboxylic acids such as toluenesulfonic acid, dodecylbenzenesulfonic acid, and benzoic acid. If the neutralization is carried out with a poorly water-soluble acid like a higher fatty acid, the product acid addition salt of an amidoamine compound will be a water-insoluble salt; thus it is undesirable because the blending into a hair conditioning composition is difficult.

The blending quantity of a cationic surfactant blended in the above-described hair conditioning composition is preferably 0.1 to 5 mass % of the total hair conditioning composition and more preferably 0.6 to 3 mass %. If the blending quantity is less than 0.1 mass %, the conditioning effect may not be achieved. If the blending quantity exceeds 5 mass %, a sticky feeling tends to be generated after use.

The above-described hair conditioning composition also contains a protein (including derivatives and hydrolyzates thereof) and/or a basic amino acid derivative.

The protein used here (including derivatives and hydrolyzates thereof) can be obtained by the extraction from plants or animals (including humans and fish) or by their hydrolysis. Those obtained by the further addition of a silyl group, a quaternary nitrogen, etc., by chemical modification, may be used. The extraction of protein can be carried out, for example, with the use of water, 1,3-butylene glycol, propylene glycol, and glycerin; however, it is not limited to these examples. The hydrolysis can be carried out with the use of for example, hydrolases and metal catalysts; however, it is not limited to these examples.

Examples of proteins (including derivatives and hydrolyzates thereof) include wool, keratin obtained from human hair and its hydrolyzates, silk protein and its silylated compounds, soybean, wheat, starch, extract from oat, protein obtained from milk, collagen and its hydrolyzates, partially hydrolyzed chitin, and hydrolyzed silk; however, it is not limited to these examples.

The blending quantity of a protein (including derivatives and hydrolyzates thereof) blended in the above-described hair conditioning composition is preferably 0.001 to 1.0 mass % as the pure protein (including derivatives and hydrolyzates thereof). If the blending quantity is less than 0.001 mass %, the conditioning effect may not be realized. If the blending quantity exceeds 1 mass %, it is undesirable from the standpoint of safety such as sensitization.

Examples of basic amino acid derivatives used in the above-described hair conditioning compositions include 3-lauryloxy-2-hydroxypropyl-L-arginine, 3-myristyloxy-2-hydroxypropyl-L-arginine, 3-myristyloxy-2-hydroxypropyl-lysine, 3-lauryloxy-2-hydroxypropyl-lysine, and 3-palmityloxy-2-hydroxypropyl-L-arginine. As a commercial product, there is Amisafe LMA-60 (manufactured by Ajinomoto Co., Inc.).

The blending quantity of a basic amino acid derivative that is blended in the above-described hair conditioning composition is preferably 0.05 to 2.0 mass % as the pure basic amino acid derivative. If the blending quantity is less than 0.05 mass %, the conditioning effect may not be realized. If the blending quantity exceeds 2.0 mass %, the stickiness may be generated.

In addition, it is preferable to further blend an oil component in the above-described hair conditioning composition. Examples of blendable oil components include liquid fat, solid fat, waxes, hydrocarbon oils, higher fatty acids, higher alcohols, synthetic ester oils, and silicone oils.

The above-described hair conditioning composition means any composition that is used on hair. In particular, however, it means a composition that provides a conditioning effect on hair. They are preferably hair conditioning compositions such as hair rinse, hair treatment, and hair pack. When the hair conditioning composition is used, it is spread well on the entire hair and washed away (rinsed off) with hot water etc.

So far, various moisturizers and oil components have been blended in the bath preparation composition to prevent post-bath skin surface dryness, improve the moisturizing effect, and smooth the skin. However, if large amounts of the moisturizers and oil components are blended, there are problems in that post-bath stickiness is generated and the light fresh feeling of the skin is lost. In addition, the remedial effect for skin itchiness and skin surface dryness is not satisfactory. When a bath preparation composition in a milky liquid form is prepared, a surfactant is normally blended to improve the stability of the base agent. However, the blending of a large amount had a trend to deteriorate the texture in use.

On the other hand, by blending the alkylene oxide derivative of the present invention in the bath preparation, a bath preparation that has a post-bath-itch improving effect and a moisturizing effect, and that causes no skin surface dryness and is excellent in the light fresh feeling, can be obtained.

In the above-described bath preparation composition, the blending quantity of the alkylene oxide derivative is normally 0.01 to 70 mass % of the total composition and preferably 0.1 to 20 mass %. If the blending quantity is less than 0.01 mass %, the manifestation of the blending effect may not be satisfactory. If the blending quantity exceeds 70 mass %, a sticky feeling may be generated after use.

In the above-described bath preparation composition, it is preferable to additionally blend a moisturizer. Examples of moisturizers include polyethylene glycol, propylene glycol, glycerin, 1,3-butylene glycol, xylitol, sorbitol, maltitol, chondroitin sulfate, hyaluronic acid, mucoitin sulfate, charonic acid, atelocollagen, cholesteryl 12-hydroxystearate, sodium lactate, bile salts, dl-pyrrolidone carboxylates, short-chain soluble collagen, diglycerin (EO)PO adduct, chestnut rose extract, yarrow extract, and melilot extract. The moisturizer is preferably a glycerin or a 1,3-butylene glycol.

The blending quantity of the moisturizer is not limited in particular; however, the blending quantity is preferably 0.001 to 20.0 mass % of the total bath preparation composition, and more preferably 0.1 to 10.0 mass %.

It is also preferable that an inorganic salt is additionally blended in the above-described bath preparation composition. Examples of inorganic salts include sodium sulfate, sodium hydrogencarbonate, sodium sesquicarbonate, sodium chloride, borax, sodium carbonate, potassium carbonate, potassium hydrogencarbonate, potassium nitrate, sodium nitrate, calcium nitrate, aluminum nitrate, sodium polyphosphate, ammonium chloride, iron sulfate, sodium phosphate, magnesium sulfate, sodium thiosulfate, sodium sulfide, calcium oxide, magnesium carbonate, and potassium chloride.

The blending quantity of inorganic salt is not limited in particular; however, the blending quantity is preferably 30.0 to 99.0 mass % of the total bath preparation composition, and more preferably 60.0 to 95.0 mass %.

The above-described bath preparation composition can be in any form, for example, powder, granules, a liquid, or a solid.

EXAMPLES

Example 1

Hereinafter, the present invention will be more concretely described by examples. However, the present invention is not limited by these examples. The blending quantity is expressed in mass % unless otherwise noted.

At first, the evaluation methods used in the present invention will be described.

Evaluation (1): Spreadability

For the spreadability on the skin during use, the actual usage test was conducted by 10 professional panelists using respective test examples. The evaluation criteria were as follows.

◎ . . . 8 or more panelists recognized that the spreadability on the skin was good during use.

○ . . . 6 or more and less than 8 panelists recognized that the spreadability on the skin was good during use.

Δ . . . 3 or more and less than 6 panelists recognized that the spreadability on the skin was good during use.

X . . . . Less than 3 panelists recognized that the spreadability on the skin was good during use.

Evaluation (2): Absence of Sticky Feeling

For the absence of sticky feeling of skin during and after use, the actual usage test was conducted by 10 professional panelists using respective test examples. The evaluation criteria were as follows.

◎ . . . 8 or more panelists recognized that the sticky feeling was not present during and after use.

○ . . . 6 or more and less than 8 panelists recognized that the sticky feeling was not present during and after use.

Δ . . . 3 or more and less than 6 panelists recognized that the sticky feeling was not present during and after use.

X . . . . Less than 3 panelists recognized that the sticky feeling was not present during and after use.

Evaluation (3): Refreshing Feeling

For the refreshing feeling of skin after use, the actual usage test was conducted by 10 professional panelists using respective test examples. The evaluation criteria were as follows.

◎ . . . 8 or more panelists recognized that the refreshing feeling was present after use.

○ . . . 6 or more and less than 8 panelists recognized that the refreshing feeling was present after use.

Δ . . . 3 or more and less than 6 panelists recognized that the refreshing feeling was present after use.

X . . . . Less than 3 panelists recognized that the refreshing feeling was present after use.

Evaluation (4): Moisturizing Effect Feeling

For the moisturizing effect feeling 120 minutes after use, the actual usage test was conducted by 10 professional panelists using respective test examples. The evaluation criteria were as follows.

◎ . . . 8 or more panelists recognized that the moisturizing effect feeling was present.

○ . . . 6 or more and less than 8 panelists recognized that the moisturizing effect feeling was present.

Δ . . . 3 or more and less than 6 panelists recognized that the moisturizing effect feeling was present.

X . . . . Less than 3 panelists recognized that the moisturizing effect feeling was present.

Evaluation (5): Rough Skin Improving Effect Test

The test for a rough skin improving effect was conducted by 10 panelists having rough skin on the face (region: cheeks) using respective test examples. The test method was as follows; different skin external preparations were applied on the right and left cheeks for a week, and the effect was judged on the next day after the end of the test period. The evaluation criteria were as follows.

◎ . . . 8 or more panelists recognized that the rough skin was improved.

○ . . . 6 or more and less than 8 panelists recognized that the rough skin was improved.

Δ . . . 3 or more and less than 6 panelists recognized that the rough skin was improved.

X . . . Less than 3 panelists recognized that the rough skin was improved.

Evaluation (6): Skin Irritation Test

A 24-hour occlusive patch test was performed on the medial side of the upper arm of 10 panelists, and then the average value was calculated based on the following criteria. The evaluation criteria were as follows.

0 . . . No abnormality was observed.

1 . . . . Slight redness was observed.

2 . . . . Redness was observed.

3 . . . . Redness and papules were observed.

The evaluation criteria of skin irritation test were as follows.

◎ . . . . The average value of 10 panelists was 0 or higher and less than 0.15.

○ . . . . The average value of 10 panelists was 0.15 or higher and less than 0.2.

Δ . . . . The average value of 10 panelists was 0.2 or higher and less than 0.3.

X . . . . The average value of 10 panelists was 0.3 or higher.

Evaluation (7): Stability of Base Agent

Each test example of the skin external preparation (lotion) was filled in a transparent glass bottle immediately after the production and allowed to stand at 50° C. for 4 weeks. Then, based on the following criteria, the evaluation of base agent stability was carried out by visual observation.

<Evaluation Criteria>

○: colorless and transparent

Δ: slightly turbid

X: white turbid or separated

<Synthesis of Alkylene Oxide Derivatives>

In the following, the synthesis method of the alkylene oxide derivative used in the present invention is shown. The addition mole numbers of oxyalkylene groups and oxyethylene groups are described by the values 2 a and 2 b, respectively.

Compound 1: POB (18 mol) POE (41 mol) Dimethyl Dimer Diol Ether $$Z-\{O-[(AO)_a-(EO)_b]-R\}_2$$

(Z: residue of the dimer diol (linoleic acid derived) having 36 carbon atoms, AO: oxybutylene group, 2 a=18, 2 b=41, R=methyl group, EO/(AO EO)=58.2 mass %)

Into an autoclave, 270 g of dimer diol (0.50 mol, product name: Sovermol 908 manufactured by Cognis Japan Ltd., dimer diol derived from linoleic acid) and 6.0 g of potassium hydroxide were loaded. After the air in the autoclave was replace with dry nitrogen, the catalyst was completely dissolved with stirring at 140° C. Subsequently, at 120° C. and 0.2 to 0.5 MPa (gauge pressure), 650 g of butylene oxide was dropwise added from a dropping apparatus and stirred for 3 hours. Subsequently, at 120° C. and 0.2 to 0.5 MPa (gauge pressure), 905 g of ethylene oxide was dropwise added from a dropping apparatus and stirred for 2 hours. Subsequently, 100 g of potassium hydroxide was loaded; after the system was replaced with dry nitrogen, 60 g of methyl chloride was pressured in at 80 to 130° C. and 0.3 MPa (gauge pressure), and the reaction was carried out for 6 hours. Then, the reactant was taken out from the autoclave, neutralized with hydrochloric acid to pH 6 to 7, and the contained water was removed by treating at 100° C. for 1 hour. After the treatment, in order to remove the formed salt, the filtration was performed and compound 1 was obtained.

According to the above synthesis example, the present inventors have prepared compounds 1 to 5 and comparative compounds 1 to 6 shown in Table 1.

TABLE 1

$Z-\{O-[(AO)_a-(EO)_b]-R\}_2$

|  | Z | $(AO)_{2/a}$ | $(EO)_{2\times b}$ | R | (AO)(EO) bond | EO/(AO + EO) (mass %) |
|---|---|---|---|---|---|---|
| Compound 1 | C36 dimer diol (oleic acid derived) residue | butylene oxide 18 mol | ethylene oxide 41 mol | $CH_3$ | block | 58.2 |
| Compound 2 | C36 dimer diol (oleic acid derived) residue | butylene oxide 21 mol | ethylene oxide 56 mol | " | " | 62.0 |
| Compound 3 | C36 dimer diol (oleic acid derived) residue | butylene oxide 25 mol | ethylene oxide 35 mol | " | " | 46.1 |
| Compound 4 | C36 dimer diol (oleic acid derived) residue | butylene oxide 40 mol | ethylene oxide 120 mol | " | " | 64.7 |
| Compound 5 | C36 dimer diol (oleic acid derived) residue | butylene oxide 70 mol | ethylene oxide 40 mol | " | " | 25.9 |
| Comparative compound 1 | C36 dimer diol (oleic acid derived) residue | — | ethylene oxide 57 mol | " | " | 100.0 |
| Comparative compound 2 | C36 dimer diol (oleic acid derived) residue | butylene oxide 34 mol | — | " | " | 0 |
| Comparative compound 3 | C36 dimer diol (oleic acid derived) residue | butylene oxide 30 mol | ethylene oxide 30 mol | H | " | 37.9 |
| Comparative compound 4 | C36 dimer diol (oleic acid derived) residue | butylene oxide 30 mol | ethylene oxide 30 mol | $C_6H_{13}$ | " | 37.9 |
| Comparative compound 5 | C36 dimer diol (oleic acid derived) residue | butylene oxide 18 mol | ethylene oxide 41 mol | $CH_3$ | random | 58.2 |
| Comparative compound 6 | 1,4-butanediol | butylene oxide 18 mol | ethylene oxide 41 mol | $CH_3$ | block | 58.2 |

<Blending into Skin External Preparation>

Subsequently, the present inventors produced skin external preparations (lotions), by a conventional method, of the respective examples and comparative examples with the blending compositions listed in Table 2 and Table 3, with the use of the above-produced compounds 1 to 5 and comparative compounds 1 to 6. The evaluation tests were conducted for the above-described evaluations (1) to (7).

TABLE 2

|  | Ex. 1-1 | Ex. 1-2 | Ex. 1-3 | Ex. 1-4 | Ex. 1-5 |
|---|---|---|---|---|---|
| (Phase A) |  |  |  |  |  |
| Compound 1 | 0.5 | — | — | — | — |
| Compound 2 | — | 0.5 | — | — | — |
| Compound 3 | — | — | 0.5 | — | — |
| Compound 4 | — | — | — | 0.5 | — |
| Compound 5 | — | — | — | — | 0.5 |
| Ethanol | 5 | 0.2 | 0.2 | 0.2 | 0.2 |
| Tocopherol acetate | 0.05 | 0.05 | 0.05 | 0.05 | 0.05 |
| Perfume | 0.1 | 0.1 | 0.1 | 0.1 | 0.1 |
| (Phase B) |  |  |  |  |  |
| Citric acid | 0.02 | 0.02 | 0.02 | 0.02 | 0.02 |
| Sodium citrate | 0.18 | 0.18 | 0.18 | 0.18 | 0.18 |
| Purified water | remainder | remainder | remainder | remainder | remainder |
| Evaluation(1) Spreadability on the skin | ⊚ | ⊚ | ⊚ | ○ | ⊚ |

TABLE 2-continued

|  | Ex. 1-1 | Ex. 1-2 | Ex. 1-3 | Ex. 1-4 | Ex. 1-5 |
|---|---|---|---|---|---|
| Evaluation(2) Absence of sticky feeling | ⊚ | ⊚ | ⊚ | ○ | ⊚ |
| Evaluation(3) Refreshing feeling | ⊚ | ⊚ | ⊚ | ○ | ⊚ |
| Evaluation(4) Moisturizing effect feeling | ⊚ | ⊚ | ⊚ | ⊚ | ○ |
| Evaluation(5) Rough skin improving effect | ⊚ | ⊚ | ⊚ | ⊚ | ○ |
| Evaluation(6) Skin irritation | ⊚ | ⊚ | ⊚ | ⊚ | ○ |
| Evaluation(7) Stability of base agent | ○ | ○ | ○ | ○ | ○ |

TABLE 3

|  | Com. Ex. 1-1 | Com. Ex. 1-2 | Com. Ex. 1-3 | Com. Ex. 1-4 | Com. Ex. 1-5 | Com. Ex. 1-6 | Com. Ex. 1-7 |
|---|---|---|---|---|---|---|---|
| (Phase A) | | | | | | | |
| Comparative compound 1 | 0.5 | — | — | — | — | — | — |
| Comparative compound 2 | — | 0.5 | — | — | — | — | — |
| Comparative compound 3 | — | — | 0.5 | — | — | — | — |
| Comparative compound 4 | — | — | — | 0.5 | — | — | — |
| Comparative compound 5 | — | — | — | — | 0.5 | — | — |
| Comparative compound 6 | — | — | — | — | — | 0.5 | — |
| POE(60) hydrogenated castor oil | — | — | — | — | — | — | 0.5 |
| Ethanol | 0.2 | 0.2 | 0.2 | 0.2 | 0.2 | 0.2 | 0.2 |
| Tocopherol acetate | 0.05 | 0.05 | 0.05 | 0.05 | 0.05 | 0.05 | 0.05 |
| Perfume | 0.1 | 0.1 | 0.1 | 0.1 | 0.1 | 0.1 | 0.1 |
| (Phase B) | | | | | | | |
| Citric acid | 0.02 | 0.02 | 0.02 | 0.02 | 0.02 | 0.02 | 0.02 |
| Sodium citrate | 0.18 | 0.18 | 0.18 | 0.18 | 0.18 | 0.18 | 0.18 |
| Purified water | remainder | remainder | remainder | remainder | remainder | remainder | remainder |
| Evaluation(1) Spreadability on the skin | △ | ○ | × | ⊚ | ⊚ | ⊚ | ○ |
| Evaluation(2) Absence of sticky feeling | △ | ○ | × | ⊚ | ⊚ | ⊚ | × |
| Evaluation(3) Refreshing feeling | △ | ○ | × | ⊚ | ⊚ | ⊚ | × |
| Evaluation(4) Moisturizing effect feeling | ○ | × | ○ | △ | ⊚ | ⊚ | △ |
| Evaluation(5) Rough skin improving effect | △ | × | △ | △ | ⊚ | ⊚ | × |
| Evaluation(6) Skin irritation | ○ | △ | △ | ○ | ⊚ | ⊚ | ○ |
| Evaluation(7) Stability of base agent | × | × | ○ | ○ | × | △ | ○ |

As shown in Table 2, Examples 1-1 to 1-5, wherein a block-type alkylene oxide/ethylene oxide-dimer diol ether with a specific structure (compounds 1 to 5) is blended, were excellent in all the evaluations (1) to (7).

On the other hand, as shown in Table 3, Comparative Examples 1-1 and 1-2, wherein a compound with only oxyethylene groups or only oxybutylene groups (comparative compounds 1 and 2) were used, did not function as a surfactant and the base agent stability was poor. In the case of only oxyethylene groups, the texture in use and the rough skin improving effect were poor. In the case of only oxybutylene groups, the moisturizing effect feeling and the rough skin improving effect could not be achieved.

In Comparative Example 1-3, wherein a compound having a hydrogen atom at both terminals (comparative compound 3) was used, the texture in use, rough skin improving effect, and skin irritation were undesirable. In Comparative Example 1-4, wherein a compound having, at both terminals, a hydrocarbon group having 6 carbon atoms (comparative compound 4) was used, the moisturizing effect feeling and the rough skin improving effect were not satisfactory.

Comparative Example 1-5, wherein a compound with the random-type bonding of alkylene oxide/ethylene oxide (comparative compound 5) was used, did not function as a surfactant and the base agent stability was poor. In Comparative Example 1-6, wherein a compound without the dimer diol skeleton (comparative compound 6) was used, the refreshing feeling was poor, the surface activity was weak, and the base agent stability was not satisfactory.

In Comparative Example 1-7, wherein POE (60) hydrogenated castor oil, which was widely used in skin external preparations in the past, was used, the texture in use was poor and the rough skin improving effect was not observed.

<Blending Quantity of Alkylene Oxide Derivative>

In order to investigate the suitable blending quantity, into the skin external preparation, of the alkylene oxide derivative of the present invention, skin external preparations (lotions) of the respective examples with the blending compositions listed in Table 4 were produced by a conventional method. The evaluation tests were conducted for the above-described evaluations (1) to (7).

TABLE 4

|  | Ex. 1-6 | Ex. 1-7 | Ex. 1-8 | Ex. 1-9 |
|---|---|---|---|---|
| (Water phase) | | | | |
| Compound 1 | 0.01 | 0.1 | 20 | 70 |
| POE (60) hydrogenated castor oil | — | — | — | — |
| Carboxy vinyl polymer | 0.2 | 0.2 | 0.2 | 0.2 |
| Potassium hydroxide | 0.1 | 0.1 | 0.1 | 0.1 |
| Sorbitol | 5 | 5 | 5 | 5 |
| Dipropylene glycol | 3 | 3 | 3 | 3 |
| Ethanol | 4 | 4 | 4 | 4 |
| Purified water | remainder | remainder | remainder | remainder |
| (Oil phase) | | | | |
| Liquid paraffin | 5 | 5 | 5 | 5 |
| Glyceryl tri-2-ethylhexanoate | 4 | 4 | 4 | 4 |
| Cetyl octanoate | 2 | 2 | 2 | 2 |
| Antiseptic agent | proper quantity | proper quantity | proper quantity | proper quantity |
| Perfume | proper quantity | proper quantity | proper quantity | proper quantity |
| Evaluation (1) Spreadability on the skin | ○ | ◎ | ◎ | ○ |
| Evaluation (2) Absence of sticky feeling | ○ | ◎ | ◎ | ○ |
| Evaluation (3) Refreshing feeling | ○ | ◎ | ◎ | ○ |
| Evaluation (4) Moisturizing effect feeling | ○ | ◎ | ◎ | ◎ |
| Evaluation (5) Rough skin improving effect | ○ | ◎ | ◎ | ◎ |
| Evaluation (6) Skin irritation | ○ | ◎ | ◎ | ◎ |
| Evaluation (7) Stability of base agent | ○ | ○ | ○ | ○ |

From Table 4, it was confirmed that when the blending quantity of the alkylene oxide derivative was in the range of 0.01 to 70 mass %, there was a rough skin improving effect, the safety was superior, and the texture in use was excellent. The safety and the rough skin improving effect increased with an increase in the blending quantity of the alkylene oxide derivative. In terms of the spreadability on the skin and the absence of sticky feeling, it is especially preferable that the blending quantity of the alkylene oxide derivative is 0.1 to 20 mass %.

Example 2

Blending into Skin Cleanser

Subsequently, the present inventors produced skin cleanser, by a conventional method, of the respective examples and comparative examples with the blending compositions listed in Table 5 and Table 6, with the use of the above-described compounds 1 to 5 and comparative compounds 1 to 6. The evaluation tests were conducted for the below-described evaluations (1) to (6).

The formulations of cosmetics (sunscreen and strong covering foundation) used for the tests and the evaluation criteria are shown in the following.

Formulation of Sunscreen

|  | (mass %) |
|---|---|
| (1) Methyl polysiloxane | 5.0 |
| (2) Decamethylcyclopentasiloxane | 20.0 |
| (3) Trimethylsiloxysilicate | 2.0 |
| (4) Polyoxyethylene/methyl polysiloxane copolymer | 1.0 |
| (5) 1,3-butylene glycol | 5.0 |
| (6) Isostearic acid | 0.3 |
| (7) Titanium oxide | 17.0 |
| (8) Octyl methoxycinnamate | 8.0 |
| (9) Clay mineral | 0.5 |
| (10) Polyalkyl acrylate | 5.0 |
| (11) Trisodium edetate | proper quantity |

-continued

|  | (mass %) |
|---|---|
| (12) Antiseptic agent | proper quantity |
| (13) Perfume | proper quantity |
| (14) Purified water | remainder |

Formulation of Foundation

|  | (mass %) |
|---|---|
| (1) Decamethylcyclopentasiloxane | 14.0 |
| (2) Octamethylcyclotetrasiloxane | 24.0 |
| (3) Siliconated pullulan | 15.0 |
| (4) Isostearic acid | 1.0 |
| (5) Titanium oxide | 5.0 |
| (6) Octyl methoxycinnamate | 5.0 |
| (7) Dextrin fatty acid coated powder | 25.0 |
| (8) Alcohol | remainder |
| (9) Purified water | proper quantity |

"Evaluation (1): Rinsability During Cleansing"

Both a sunscreen and a strong covering foundation were applied, the face was cleansed with a test sample after 2 hours, and the actual usage test by 10 professional panelists, for the rinsability during cleansing, was conducted. The score based on the below-described rating criteria was determined. Here, the score was determined by setting the score of the control skin cleanser (comprising POE(10) isostearic acid) to be zero. The average value was calculated by dividing the sum of scores of each panelist by the number of panelists, and the evaluation results were obtained based on the below-described evaluation criteria.

+3: Very good rinsability was recognized compared with the control skin cleanser.
+2: Good rinsability was recognized compared with the control skin cleanser.
+1: Some rinsability was recognized compared with the control skin cleanser.
0: Neither applies.

−1: The rinsability was hardly present compared with the control skin cleanser.
−2: No rinsability was present compared was recognized with the control skin cleanser.
−3: Absolutely no rinsability was present compared with the control skin cleanser.
Evaluation Criteria
A: The average value of 10 panelists was +1.5 points or higher.
B: The average value of 10 panelists was 0 point or higher and less than 1.5 points.
C: The average value of 10 panelists was −1.5 points or higher and less than 0 point.
D: The average value of 10 panelists was less than −1.5 points.

"Evaluation (2): Smoothness after Cleansing"

Both a sunscreen and a strong covering foundation were applied, the face was cleansed with a test sample after 2 hours, and the actual usage test by 10 professional panelists, for the smoothness after cleansing, was conducted. The score based on the below-described rating criteria was determined. Here, the score was determined by setting the score of the control skin cleanser (comprising POE(10) isostearic acid) to be zero. The average value was calculated by dividing the sum of scores of each panelist by the number of panelists, and the evaluation results were obtained based on the below-described evaluation criteria.
+3: A significant smoothness was recognized compared with the control skin cleanser.
+2: A smoothness was recognized compared with the control skin cleanser.
+1: Some smoothness was recognized compared with the control skin cleanser.
0: Neither applies.
−1: Almost no smoothness was present compared with the control skin cleanser.
−2: No smoothness was present compared was recognized with the control skin cleanser.
−3: Absolutely no smoothness was present compared with the control skin cleanser.
Evaluation Criteria
A: The average value of 10 panelists was +1.5 points or higher.
B: The average value of 10 panelists was 0 point or higher and less than 1.5 points.
C: The average value of 10 panelists was −1.5 points or higher and less than 0 point.
D: The average value of 10 panelists was less than −1.5 points.

"Evaluation (3): Light Fresh Feeling after Cleansing"

Both a sunscreen and a strong covering foundation were applied, the face was cleansed with a test sample after 2 hours, and the actual usage test by 10 professional panelists, for the light fresh feeling after cleansing, was conducted. The score based on the below-described rating criteria was determined. Here, the score was determined by setting the score of the control skin cleanser (comprising POE(10) isostearic acid) to be zero. The average value was calculated by dividing the sum of scores of each panelist by the number of panelists, and the evaluation results were obtained based on the below-described evaluation criteria.
+3: A significant light fresh feeling was recognized after cleansing compared with the control skin cleanser.
+2: A light fresh feeling was recognized after cleansing compared with the control skin cleanser.
+1: Some light fresh feeling was recognized after cleansing compared with the control skin cleanser.
0: Neither applies.
−1: Almost no light fresh feeling was present after cleansing compared with the control skin cleanser.
−2: No light fresh feeling was present after cleansing compared was recognized with the control skin cleanser.
−3: Absolutely no light fresh feeling was present after cleansing compared with the control skin cleanser.
Evaluation Criteria
A: The average value of 10 panelists was +1.5 points or higher.
B: The average value of 10 panelists was 0 point or higher and less than 1.5 points.
C: The average value of 10 panelists was −1.5 points or higher and less than 0 point.
D: The average value of 10 panelists was less than −1.5 points.

"Evaluation (4): Frictional Feeling after Cleansing"

Both a sunscreen and a strong covering foundation were applied, the face was cleansed with a test sample after 2 hours, and the actual usage test by 10 professional panelists, for the frictional feeling after cleansing, was conducted. The score based on the below-described rating criteria was determined. Here, the score was determined by setting the score of the control skin cleanser (comprising POE(10) isostearic acid) to be zero. The average value was calculated by dividing the sum of scores of each panelist by the number of panelists, and the evaluation results were obtained based on the below-described evaluation criteria.
+3: Absolutely no frictional feeling was recognized after cleansing compared with the control skin cleanser.
+2: No frictional feeling was recognized after cleansing compared was recognized with the control skin cleanser.
+1: Almost no frictional feeling was recognized after cleansing compared with the control skin cleanser.
0: Neither applies.
−1: Some frictional feeling was present after cleansing compared with the control skin cleanser.
−2: A frictional feeling was present after cleansing compared with the control skin cleanser.
−3: A significant frictional feeling was present after cleansing compared with the control skin cleanser.
Evaluation Criteria
A: The average value of 10 panelists was +1.5 points or higher.
B: The average value of 10 panelists was 0 point or higher and less than 1.5 points.
C: The average value of 10 panelists was −1.5 points or higher and less than 0 point.
D: The average value of 10 panelists was less than −1.5 points.

"Evaluation (5): Cosmetic-Removal Effect"

Both a sunscreen and a strong covering foundation were applied, the face was cleansed with a test sample after 2 hours, and the actual usage test by 10 professional panelists, for the cosmetic-removal effect after cleansing, was conducted. The score based on the below-described rating criteria was determined. Here, the score was determined by setting the score of the control skin cleanser (comprising POE(10) isostearic acid) to be zero. The average value was calculated by dividing the sum of scores of each panelist by the number of panelists, and the evaluation results were obtained based on the below-described evaluation criteria.
+3: A very high cosmetic-removal effect was recognized after cleansing compared with the control skin cleanser.
+2: A high cosmetic-removal effect was recognized after cleansing compared with the control skin cleanser.
+1: Somewhat high cosmetic-removal effect was recognized after cleansing compared with the control skin cleanser.
0: Neither applies.

−1: Somewhat low cosmetic-removal effect was recognized after cleansing compared with the control skin cleanser.
−2: A low cosmetic-removal effect was recognized after cleansing compared with the control skin cleanser.
−3: A very low cosmetic-removal effect was recognized after cleansing compared with the control skin cleanser.

Evaluation Criteria

A: The average value of 10 panelists was +1.5 points or higher.
B: The average value of 10 panelists was 0 point or higher and less than 1.5 points.
C: The average value of 10 panelists was −1.5 points or higher and less than 0 point.
D: The average value of 10 panelists was less than −1.5 points.

"Evaluation (6): Skin Irritation Test"

A 24-hour occlusive patch test was performed on the medial side of the upper arm of 10 subjects, and then the average value was calculated based on the following rating criteria. The evaluation criteria were as follows.

Rating Criteria 0 point: No abnormality was observed.
1 point: Slight redness was observed.
2 points: Redness was observed.
3 points: Redness and papules were observed.

Evaluation Criteria

A: The average value of 10 panelists was less than 0.15 points.
B: The average value of 10 panelists was 0.15 points or higher and less than 0.2 points.
C: The average value of 10 panelists was 0.2 points or higher and less than 0.3 points.
D: The average value of 10 panelists was 0.3 points or higher.

TABLE 5

|  | control | Ex. 2-1 | Ex. 2-2 | Ex. 2-3 | Ex. 2-4 | Ex. 2-5 |
| --- | --- | --- | --- | --- | --- | --- |
| Carboxy vinyl polymer | 0.5 | 0.5 | 0.5 | 0.5 | 0.5 | 0.5 |
| Hydroxyethyl cellulose | 0.02 | 0.02 | 0.02 | 0.02 | 0.02 | 0.02 |
| Acrylic acid/alkyl methacrylate copolymer | 0.1 | 0.1 | 0.1 | 0.1 | 0.1 | 0.1 |
| Decamethylcyclopentasiloxane | 10 | 10 | 10 | 10 | 10 | 10 |
| Liquid paraffin | 3 | 3 | 3 | 3 | 3 | 3 |
| POE(10) isostearic acid | 5 | — | — | — | — | — |
| Compound 1 | — | 5 | — | — | — | — |
| Compound 2 | — | — | 5 | — | — | — |
| Compound 3 | — | — | — | 5 | — | — |
| Compound 4 | — | — | — | — | 5 | — |
| Compound 5 | — | — | — | — | — | 5 |
| Dipropylene glycol | 5 | 5 | 5 | 5 | 5 | 5 |
| Potassium hydroxide | proper quantity | proper quantity | proper quantity | proper quantity | proper quantity | proper quantity |
| Perfume | proper quantity | proper quantity | proper quantity | proper quantity | proper quantity | proper quantity |
| Purified water | remainder | remainder | remainder | remainder | remainder | remainder |
| Evaluation(1) Rinsability during cleansing | — | A | A | A | A | A |
| Evaluation(2) Smoothness after cleansing | — | A | A | A | B | A |
| Evaluation(3) Light fresh feeling after cleansing | — | A | A | A | B | B |
| Evaluation(4) Frictional feeling after cleansing | — | A | A | A | A | B |
| Evaluation(5) Cosmetic removing effect | — | A | A | A | A | B |
| Evaluation(6) Skin irritation test | — | A | A | A | A | B |

TABLE 6

|  | control | Com. Ex. 2-1 | Com. Ex. 2-2 | Com. Ex. 2-3 | Com. Ex. 2-4 | Com. Ex. 2-5 | Com. Ex. 2-6 |
| --- | --- | --- | --- | --- | --- | --- | --- |
| Carboxy vinyl polymer | 0.5 | 0.5 | 0.5 | 0.5 | 0.5 | 0.5 | 0.5 |
| Hydroxyethyl cellulose | 0.02 | 0.02 | 0.02 | 0.02 | 0.02 | 0.02 | 0.02 |
| Acrylic acid/alkyl methacrylate copolymer | 0.1 | 0.1 | 0.1 | 0.1 | 0.1 | 0.1 | 0.1 |
| Decamethylcyclopentasiloxane | 10 | 10 | 10 | 10 | 10 | 10 | 10 |
| Liquid paraffin | 3 | 3 | 3 | 3 | 3 | 3 | 3 |
| POE(10) isostearic acid | 5 | — | — | — | — | — | — |
| Comparative compound 1 | — | 5 | — | — | — | — | — |
| Comparative compound 2 | — | — | 5 | — | — | — | — |
| Comparative compound 3 | — | — | — | 5 | — | — | — |
| Comparative compound 4 | — | — | — | — | 5 | — | — |
| Comparative compound 5 | — | — | — | — | — | 5 | — |
| Comparative compound 6 | — | — | — | — | — | — | 5 |
| Dipropylene glycol | 5 | 5 | 5 | 5 | 5 | 5 | 5 |
| Potassium hydroxide | proper quantity | proper quantity | proper quantity | proper quantity | proper quantity | proper quantity | proper quantity |
| Perfume | proper quantity | proper quantity | proper quantity | proper quantity | proper quantity | proper quantity | proper quantity |

TABLE 6-continued

|  | control | Com. Ex. 2-1 | Com. Ex. 2-2 | Com. Ex. 2-3 | Com. Ex. 2-4 | Com. Ex. 2-5 | Com. Ex. 2-6 |
|---|---|---|---|---|---|---|---|
| Purified water | remainder | remainder | remainder | remainder | remainder | remainder | remainder |
| Evaluation(1) Rinsability during cleansing | — | C | D | C | A | A | A |
| Evaluation(2) Smoothness after cleansing | — | B | A | C | A | B | B |
| Evaluation(3) Light fresh feeling after cleansing | — | C | B | B | C | C | B |
| Evaluation(4) Frictional feeling after cleansing | — | C | C | C | C | B | C |
| Evaluation(5) Cosmetic removing effect | — | C | C | A | A | C | B |
| Evaluation(6) Skin irritation test | — | B | B | C | B | A | A |

As shown in Table 5, Examples 2-1 to 2-5, wherein a block-type alkylene oxide/ethylene oxide-dimer diol ether with a specific structure (compounds 1 to 5) and dipropylene glycol were blended, were excellent in all the evaluations (1) to (6) compared with the conventional skin cleanser with potassium POE (10) isostearate.

On the other hand, as shown in Table 6, Comparative Examples 2-1 and 2-2, wherein a compound containing only oxyethylene groups or only oxybutylene groups (comparative compounds 1 and 2) were used, did not function as a surfactant and the cosmetic-removal effect was poor. In the case of oxyethylene groups only, the rinsability during cleansing, light fresh feeling after cleansing, and the frictional feeling after cleansing were poor. In the case of oxybutylene groups only, the rinsability during cleansing and the frictional feeling after cleansing were not satisfactory.

In Comparative Example 2-3, wherein a compound having a hydrogen atom at both terminals (comparative compound 3) was used, the rinsability during cleansing, smoothness after cleansing, frictional feeling, and skin irritation were undesirable. In Comparative Example 2-4, wherein a compound having a hydrocarbon group having 6 carbon atoms at both terminals (comparative compound 4) was used, the light fresh feeling after cleansing and frictional feeling were not satisfactory.

In Comparative Example 2-5, wherein a compound with the random-type bonding of the alkylene oxide/ethylene oxide (comparative compound 5) was used, the light fresh feeling after cleansing was poor. In addition, the function as a surfactant was poor; as a result, the cosmetic-removal effect was particularly unsatisfactory. In Comparative Example 2-6, wherein an alkylene oxide/ethylene oxide derivative without the dimer diol section (comparative compound 6) was used, the frictional feeling after cleansing was particularly unsatisfactory.

As is clear from the above results, by blending a combination of a block-type alkylene oxide derivative with a specific structure and dipropylene glycol into a skin cleanser, a skin cleanser having a good texture in use, especially excellent rinsability during cleansing, a light fresh feeling after cleansing, no frictional feeling, a high cosmetic cleansing effect, and low skin irritation could be obtained.

In the following, the combination effect with a moisturizer to the skin cleanser was investigated. The results are shown in Table 7.

TABLE 7

|  | Ex. 2-1 | Ex. 2-6 | Com. Ex. 2-7 | Com. Ex. 2-8 | Com. Ex. 2-9 |
|---|---|---|---|---|---|
| Carboxy vinyl polymer | 0.5 | 0.5 | 0.5 | 0.5 | 0.5 |
| Hydroxyethyl cellulose | 0.02 | 0.02 | 0.02 | 0.02 | 0.02 |
| Acrylic acid/alkyl methacrylate copolymer | 0.1 | 0.1 | 0.1 | 0.1 | 0.1 |
| Decamethylcyclopentasiloxane | 10 | 10 | 10 | 10 | 10 |
| Liquid paraffin | 3 | 3 | 3 | 3 | 3 |
| Compound 1 | 5 | 5 | 5 | — | 5 |
| Dipropylene glycol | 5 | 2.5 | — | 5 | — |
| Glycerin | — | 2.5 | — | — | — |
| Polyethylene glycol(molecular weight 400) | — | — | 5 | — | — |
| Potassium hydroxide | proper quantity | proper quantity | proper quantity | proper quantity | proper quantity |
| Perfume | proper quantity | proper quantity | proper quantity | proper quantity | proper quantity |
| Purified water | remainder | remainder | remainder | remainder | remainder |
| Evaluation(1) Rinsability during cleansing | A | A | A | C | B |
| Evaluation(2) Smoothness after cleansing | A | A | B | D | B |
| Evaluation(3) Light fresh feeling after cleansing | A | A | A | B | A |
| Evaluation(4) Frictional feeling after cleansing | A | A | C | C | C |
| Evaluation(5) Cosmetic removing effect | A | A | A | D | B |
| Evaluation(6) Skin irritation test | A | A | A | C | A |

As shown in Table 7, in Examples 2-1 and 2-6, wherein a block-type alkylene oxide/ethylene oxide-dimer diol ether with a specific structure (compound 1) and dipropylene glycol and/or glycerin were blended, all the evaluations (1) to (6) were excellent.

On the other hand, when polyethylene glycol (molecular weight: 400) was used as the moisturizer component (Comparative Example 2-7) or when a moisturizer component was not blended (Comparative Example 2-9), the frictional feeling after cleansing was particularly unsatisfactory. When an alkylene oxide derivative was not blended (Comparative Example 2-8), it was observed to be poor in all the evaluations, namely, the texture in use, cosmetic-removal effect, and skin irritation.

In the following, the preferable blending quantity of the alkylene oxide derivative in the skin cleanser was investigated, and the results are shown in Table 8.

TABLE 8

|  | Ex. 2-7 | Ex. 2-8 | Ex. 2-9 | Ex. 2-10 |
|---|---|---|---|---|
| Carboxy vinyl polymer | 0.5 | 0.5 | 0.5 | 0.5 |
| Hydroxyethyl cellulose | 0.02 | 0.02 | 0.02 | 0.02 |
| Acrylic acid/alkyl methacrylate copolymer | 0.1 | 0.1 | 0.1 | 0.1 |
| Decamethylcyclopentasiloxane | 10 | 10 | 10 | 10 |
| Liquid paraffin | 3 | 3 | 3 | 3 |
| Compound 1 | 0.1 | 1 | 10 | 20 |
| Dipropylene glycol | 2.5 | 2.5 | 2.5 | 2.5 |
| Glycerin | 2.5 | 2.5 | 2.5 | 2.5 |
| Potassium hydroxide | proper quantity | proper quantity | proper quantity | proper quantity |
| Perfume | proper quantity | proper quantity | proper quantity | proper quantity |
| Purified water | remainder | remainder | remainder | remainder |
| Evaluation (1) Rinsability during cleansing | B | A | A | B |
| Evaluation (2) Smoothness after cleansing | B | A | A | A |
| Evaluation (3) Light fresh feeling after cleansing | B | A | A | B |
| Evaluation (4) Frictional feeling after cleansing | B | A | A | A |
| Evaluation (5) Cosmetic removing effect | B | A | A | A |
| Evaluation (6) Skin irritation test | B | A | A | B |

As seen from the results in Table 8, the blending effect of the block-type alkylene oxide/ethylene oxide-dimer diol ether with a specific structure could be recognized from about 0.1 mass %. However, the blending effect became prominent at 1.0 mass % or higher. However, if the blending quantity was 20 mass % or higher, it was difficult to sense a light fresh feeling after cleansing, etc. Thus, the blending up to about 10 mass % is especially preferable.

Example 3

Blending into Hair Conditioning Composition

Subsequently, the present inventors produced hair conditioning compositions, by a conventional method, of the respective examples and comparative examples with the blending compositions listed in Tables 9 to 11, with the use of the above-described compounds 1 to 5 and comparative compounds 1 to 6. The evaluation tests were conducted for the below-described evaluations (1) to (5).

The hair conditioning composition (rinse) that was used as a control in each test and the evaluation criteria are shown below.

Formulation of control hair conditioning composition (rinse)

| Components | (mass %) |
|---|---|
| (1) Stearyltrimethylammonium chloride | 1.0 |
| (2) Cetostearyl alcohols (C16/C18 = 7/3) | 7.0 |
| (3) Dimethyl polysiloxane (20 cs) | 5.0 |
| (4) Dipropylene glycol | 6.0 |
| (5) Antiseptic agent | proper quantity |
| (6) Pigment | proper quantity |
| (7) Perfume | proper quantity |
| (8) Purified water | remainder |

Evaluation (1): Light Rustling Feeling after Use

The actual usage test by 10 professional panelists was conducted by comparing with the control hair conditioning composition, and the light rustling feeling of hair after use (after drying), was scored according to the below-described rating criteria. Here, the score was determined by setting the score of the control hair conditioning composition to be zero. The average value was calculated by dividing the sum of scores of each panelist by the number of panelists, and the evaluation results were obtained based on the below-described evaluation criteria.

Rating Criteria

+3: There is a very light rustling feeling compared with the control hair conditioning composition.

+2: There is a light rustling feeling compared with the control hair conditioning composition.

+1: There is some light rustling feeling compared with the control hair conditioning composition.

0: Neither applies.

−1: There is hardly a light rustling feeling compared with the control hair conditioning composition.

−2: There is no light rustling feeling compared with the control hair conditioning composition.

−3: There is absolutely no light rustling feeling compared with the control hair conditioning composition.

Evaluation Criteria

A: The average value of 10 panelists was +1.5 points or higher.

B: The average value of 10 panelists was 0 point or higher and less than 1.5 points.

C: The average value of 10 panelists was −1.5 points or higher and less than 0 point.

D: The average value of 10 panelists was less than −1.5 points.

Evaluation (2): Moist Feeling after Use

The actual usage test by 10 professional panelists was conducted by comparing with the control hair conditioning composition, and the moist feeling of hair after use (after drying), was scored according to the below-described rating criteria. Here, the score was determined by setting the score of the control hair conditioning composition to be zero. The average value was calculated by dividing the sum of scores of each panelist by the number of panelists, and the evaluation results were obtained based on the below-described evaluation criteria.

Rating Criteria

+3: There is a very moist feeling compared with the control hair conditioning composition.
+2: There is a moist feeling compared with the control hair conditioning composition.
+1: There is some moist feeling compared with the control hair conditioning composition.
0: Neither applies.
−1: There is hardly a moist feeling compared with the control hair conditioning composition.
−2: There is no moist feeling compared with the control hair conditioning composition.
−3: There is absolutely no moist feeling compared with the control hair conditioning composition.

Evaluation Criteria

A: The average value of 10 panelists was +1.5 points or higher.
B: The average value of 10 panelists was 0 point or higher and less than 1.5 points.
C: The average value of 10 panelists was −1.5 points or higher and less than 0 point.
D: The average value of 10 panelists was less than −1.5 points.

Evaluation (3): Smooth Feeling and Combing Smoothness

The actual usage test by 10 professional panelists was conducted by comparing with the control hair conditioning composition, and the smooth feeling and the combing smoothness of hair, during use and after use (after drying), were scored according to the below-described rating criteria. Here, the score was determined by setting the score of the control hair conditioning composition to be zero. The average value was calculated by dividing the sum of scores of each panelist by the number of panelists, and the evaluation results were obtained based on the below-described evaluation criteria.

Rating Criteria

+3: There is a very smooth feeling and also a feeling that the combing smoothness is good compared with the control hair conditioning composition.
+2: There is a smooth feeling and also a feeling that the combing smoothness is good compared with the control hair conditioning composition.
+1: There is some smooth feeling and also a feeling that the combing smoothness is good compared with the control hair conditioning composition.
0: Neither applies.
−1: There is hardly a smooth feeling and also a feeling that the combing smoothness is a little poor compared with the control hair conditioning composition.
−2: There is no smooth feeling and also a feeling that the combing smoothness is poor compared with the control hair conditioning composition.
−3: There is absolutely no smooth feeling and also a feeling that the combing smoothness is very poor compared with the control hair conditioning composition.

Evaluation Criteria

A: The average value of 10 panelists was +1.5 points or higher.
B: The average value of 10 panelists was 0 point or higher and less than 1.5 points.
C: The average value of 10 panelists was −1.5 points or higher and less than 0 point.
D: The average value of 10 panelists was less than −1.5 points.

Evaluation (4): Supple Feeling

The actual usage test by 10 professional panelists was conducted by comparing with the control hair conditioning composition, and the supple feeling, during use and after use (after drying), was scored according to the below-described rating criteria. Here, the score was determined by setting the score of the control hair conditioning composition to be zero. The average value was calculated by dividing the sum of scores of each panelist by the number of panelists, and the evaluation results were obtained based on the below-described evaluation criteria.

Rating Criteria

+3: There is a very supple feeling compared with the control hair conditioning composition.
+2: There is a supple feeling compared with the control hair conditioning composition.
+1: There is some supple feeling compared with the control hair conditioning composition.
0: Neither applies.
−1: There is hardly a supple feeling compared with the control hair conditioning composition.
−2: There is no supple feeling compared with the control hair conditioning composition.
−3: There is absolutely no supple feeling compared with the control hair conditioning composition.

Evaluation Criteria

A: The average value of 10 panelists was +1.5 points or higher.
B: The average value of 10 panelists was 0 point or higher and less than 1.5 points.
C: The average value of 10 panelists was −1.5 points or higher and less than 0 point.
D: The average value of 10 panelists was less than −1.5 points.

Evaluation (5): Elastic Feeling after Use

The actual usage test by 10 professional panelists was conducted by comparing with the control hair conditioning composition, and the elastic hair feeling after use (after drying), was scored according to the below-described rating criteria. Here, the score was determined by setting the score of the control hair conditioning composition to be zero. The average value was calculated by dividing the sum of scores of each panelist by the number of panelists, and the evaluation results were obtained based on the below-described evaluation criteria.

Rating Criteria

+3: There is a very elastic feeling compared with the control hair conditioning composition.
+2: There is a elastic feeling compared with the control hair conditioning composition.
+1: There is some elastic feeling compared with the control hair conditioning composition.
0: Neither applies.
−1: There is hardly a elastic feeling compared with the control hair conditioning composition.
−2: There is no elastic feeling compared with the control hair conditioning composition.
−3: There is absolutely no elastic feeling compared with the control hair conditioning composition.

Evaluation Criteria

A: The average value of 10 panelists was +1.5 points or higher.
B: The average value of 10 panelists was 0 point or higher and less than 1.5 points.
C: The average value of 10 panelists was −1.5 points or higher and less than 0 point.
D: The average value of 10 panelists was less than −1.5 points.

First, the results of the comparison tests between the conventional hair conditioning compositions and the hair conditioning compositions blended with the alkylene oxide derivative having a specific structure are shown in Table 9.

texture in use was obtained compared with the control hair conditioning composition. However, it was not sufficiently satisfactory, and a problem remained especially in the after-use elastic hair feeling.

In Comparative Example 3-4, wherein an alkylene oxide derivative (random-type) represented by $CH_3O-[(EO)_{10}/(PO)_{10}]CH_3$ was blended, roughly good evaluation results were obtained. However, in Example 3-1 and Example 3-2, wherein a structurally different block-type alkylene oxide/ethylene oxide-dimer diol ether with a specific structure was

TABLE 9

|  | Com. Ex. 3-1 | Com. Ex. 3-2 | Com. Ex. 3-3 | Com. Ex. 3-4 | Ex. 3-1 | Ex. 3-2 |
|---|---|---|---|---|---|---|
| Compound 1 | — | — | — | — | 5 | 5 |
| $CH_3O[(EO)_{10}/(PO)_{10}]CH_3$ (random polymer) | — | — | — | 5 | — | — |
| Soybean lecithin | — | — | — | 0.5 | — | — |
| 4-guanidino butyl lauramide | 2 | — | — | — | — | — |
| Monoglyceride stearate | — | 0.5 | — | — | — | — |
| Palmitic acid | — | 1.2 | — | — | — | — |
| Bis(octadecyl-N-hydroxyethyl imidazoline) chloroacetate complex | — | — | 1.5 | — | — | — |
| Stearyltrimethyl ammonium chloride | — | — | — | 1 | 1 | — |
| Behenic acid diethylaminoethylamide | 0.2 | 1.5 | 1 | — | — | 1 |
| Hydrolyzed wool keratin solution※1 | 0.2 | — | — | — | 0.5 | 0.5 |
| Cetanol | 7 | 7 | 7 | 7 | 7 | 7 |
| Dimethyl polysiloxane(20 cs) | 5 | 5 | 5 | 5 | 5 | 5 |
| Dipropylene glycol | 6 | 6 | 6 | 6 | 6 | 6 |
| Antiseptic agent | proper quantity | proper quantity | proper quantity | proper quantity | proper quantity | proper quantity |
| Pigment | proper quantity | proper quantity | proper quantity | proper quantity | proper quantity | proper quantity |
| Perfume | proper quantity | proper quantity | proper quantity | proper quantity | proper quantity | proper quantity |
| Purified water | remainder | remainder | remainder | remainder | remainder | remainder |
| Evaluation(1) Light rustling feeling after use | B | A | B | A | A | A |
| Evaluation(2) Moist feeling after use | A | B | B | A | A | A |
| Evaluation(3) Smooth feeling and Combing smoothness | A | B | B | A | A | A* |
| Evaluation(4) Supple feeling | B | A | A | A | A | A |
| Evaluation(5) Elastic feeling after use | C | C | C | B | B | A* |

※1: Promoise WK-8 (manufactured by Seiwa Kasei Co., Ltd.)
A*: The average value was +2.5 points or higher.

As is clear from the results in Table 9, in Comparative Examples 3-1 to 3-3, wherein other active components were blended, to provide a hair conditioning effect, to the hair conditioning composition in which a conventional cationic surfactant is used as the active component, a relatively good texture in use was obtained compared with the control hair conditioning composition. However, it was not sufficiently satisfactory, and a problem remained especially in the after-use elastic hair feeling.

blended, extremely good evaluation results were obtained especially in elastic hair feeling.

Based on the above results, the present inventors have further studied the alkylene oxide derivatives that are to be blended in the hair conditioning composition. The results are shown in Tables 10 and 11.

TABLE 10

|  | Ex. 3-3 | Ex. 3-4 | Ex. 3-5 | Ex. 3-6 | Ex. 3-7 |
|---|---|---|---|---|---|
| Compound 1 | 5 | — | — | — | — |
| Compound 2 | — | 5 | — | — | — |
| Compound 3 | — | — | 5 | — | — |
| Compound 4 | — | — | — | 5 | — |
| Compound 5 | — | — | — | — | 5 |
| Basic amino-acid derivative salt※2 | 1 | 1 | 1 | 1 | 1 |
| Stearyltrimethyl ammonium chloride | 1 | 1 | 1 | 1 | 1 |
| Cetostearyl Alcohol(C16/C18 = 7/3) | 7 | 7 | 7 | 7 | 7 |
| Dimethyl polysiloxane(20 cs) | 5 | 5 | 5 | 5 | 5 |
| Dipropylene glycol | 6 | 6 | 6 | 6 | 6 |
| Antiseptic agent | proper quantity | proper quantity | proper quantity | proper quantity | proper quantity |
| Pigment | proper quantity | proper quantity | proper quantity | proper quantity | proper quantity |
| Perfume | proper quantity | proper quantity | proper quantity | proper quantity | proper quantity |
| Purified water | remainder | remainder | remainder | remainder | remainder |

TABLE 10-continued

|  | Ex. 3-3 | Ex. 3-4 | Ex. 3-5 | Ex. 3-6 | Ex. 3-7 |
|---|---|---|---|---|---|
| Evaluation(1) Light rustling feeling after use | A | A | A | A | A |
| Evaluation(2) Moist feeling after use | A | A | A | A | A |
| Evaluation(3) Smooth feeling and Combing smoothness | A* | A* | A* | A | B |
| Evaluation(4) Supple feeling | A | A | A | A | B |
| Evaluation(5) Elastic feeling after use | A* | A* | A* | A | A |

※2: Amisafe LMA-60 (manufactured by Ajinomoto Co., Inc.); N-[3-alkyl(12,14)oxy-2-hydroxypropyl]-arginine hydrochloride 60% aqueous solution
A*: The average value was +2.5 points or higher.

TABLE 11

|  | Com. Ex. 3-5 | Com. Ex. 3-6 | Com. Ex. 3-7 | Com. Ex. 3-8 | Com. Ex. 3-9 | Com. Ex. 3-10 |
|---|---|---|---|---|---|---|
| Comparative compound 1 | 5 | — | — | — | — | — |
| Comparative compound 2 | — | 5 | — | — | — | — |
| Comparative compound 3 | — | — | 5 | — | — | — |
| Comparative compound 4 | — | — | — | 5 | — | — |
| Comparative compound 5 | — | — | — | — | 5 | — |
| Comparative compound 6 | — | — | — | — | — | 5 |
| Stearyltrimehyl ammonium chloride | 1 | 1 | 1 | 1 | 1 | 1 |
| Cetostearyl Alcohol(C16/C18 = 7/3) | 7 | 7 | 7 | 7 | 7 | 7 |
| Dimethyl polysiloxane(20 cs) | 5 | 5 | 5 | 5 | 5 | 5 |
| Dipropylene glycol | 6 | 6 | 6 | 6 | 6 | 6 |
| Antiseptic agent | proper quantity | proper quantity | proper quantity | proper quantity | proper quantity | proper quantity |
| Pigment | proper quantity | proper quantity | proper quantity | proper quantity | proper quantity | proper quantity |
| Perfume | proper quantity | proper quantity | proper quantity | proper quantity | proper quantity | proper quantity |
| Purified water | remainder | remainder | remainder | remainder | remainder | remainder |
| Evaluation(1) Light rustling feeling after use | C | D | C | A | A | B |
| Evaluation(2) Moist feeling after use | A | D | A | C | A | B |
| Evaluation(3) Smooth feeling and Combing smoothness | C | B | C | C | A | B |
| Evaluation(4) Supple feeling | B | C | A | A | A | B |
| Evaluation(5) Elastic feeling after use | C | C | A | B | C | C |

※2: Amisafe LMA-60 (manufactured by Ajinomoto Co., Inc.); N-[3-alkyl(12,14)oxy-2-hydroxypropyl]-arginine hydrochloride 60% aqueous solution
A*: The average value was +2.5 points or higher.

As shown in Table 10, in Examples 3-3 to 3-7, wherein a block-type alkylene oxide/ethylene oxide-dimer diol ether with a specific structure (compounds 1 to 5) was blended, they were excellent in all the evaluations (1) to (5) compared with the conventional hair conditioning composition.

On the other hand, as shown in Table 11, Comparative Example 3-5, wherein a compound with only oxyethylene groups (comparative compound 1) was used, was poor in the light rustling feeling, smooth feeling, combing smoothness, and elastic feeling. In Comparative Example 3-6, wherein a compound with only oxybutylene groups (comparative compound 2) was used, the light rustling feeling and moist feeling were especially poor, and the supple feeling and elastic feeling were also poor.

In Comparative Example 3-7, wherein a compound having a hydrogen atom at the terminal of the alkylene oxide derivative (comparative compound 3) was blended, the light rustling feeling, smooth feeling, and combing smoothness were not satisfactory. In Comparative Example 3-8, wherein a compound having a hydrocarbon group having 6 carbon atoms at the terminal of the alkylene oxide derivative (comparative compound 4) was blended, the light rustling feeling, smooth feeling, and combing smoothness were not satisfactory.

In Comparative Example 3-9, wherein a random-type alkylene oxide derivative (comparative compound 5) was blended, the elastic feeling was not sufficiently satisfactory. In Comparative Example 3-10, wherein a block-type alkylene oxide/ethylene oxide derivative without the dimer diol section (comparative compound 6) was used, the elastic feeling was especially poor.

As is clear from the above results, when a block-type alkylene oxide/ethylene oxide-dimer diol ether with a specific structure is blended in a hair conditioning composition, it is possible to obtain a hair conditioning composition having no sticky feeling before and after use and being excellent in the moist feeling, smooth feeling, supple feeling, and elastic feeling.

Subsequently, the present inventors investigated the preferable blending quantity of the alkylene oxide derivative with a specific structure. The results are shown in Table 12.

TABLE 12

|  | Ex. 3-8 | Ex. 3-9 | Ex. 3-10 | Ex. 3-11 |
|---|---|---|---|---|
| Compound 6 | 0.01 | 0.1 | 5 | 10 |
| Stearyltrimethyl ammonium chloride | 1 | 1 | 1 | 1 |
| Hydrolyzed wool keratin solution ※1 | 0.1 | 0.1 | 0.1 | 0.1 |

TABLE 12-continued

|  | Ex. 3-8 | Ex. 3-9 | Ex. 3-10 | Ex. 3-11 |
|---|---|---|---|---|
| Basic amino-acid derivative salt ※2 | 0.5 | 0.5 | 0.5 | 0.5 |
| Cetostearyl Alcohol (C16/C18 = 7/3) | 7 | 7 | 7 | 7 |
| Dimethyl polysiloxane (20 cs) | 5 | 5 | 5 | 5 |
| Dipropylene glycol | 6 | 6 | 6 | 6 |
| Antiseptic agent | proper quantity | proper quantity | proper quantity | proper quantity |
| Pigment | proper quantity | proper quantity | proper quantity | proper quantity |
| Perfume | proper quantity | proper quantity | proper quantity | proper quantity |
| Purified water | remainder | remainder | remainder | remainder |
| Evaluation (1) Light rustling feeling after use | A | A | A | B |
| Evaluation (2) Moist feeling after use | A | A | A | B |
| Evaluation (3) Smooth feeling and Combing smoothness | B | A* | A* | A |
| Evaluation (4) Supple feeling | A | A | A | A |
| Evaluation (5) Elastic feeling after use | B | A* | A* | A |

※1 Promoise WK-8 (manufactured by Seiwa Kasei Co., Ltd.)
※2 Amisafe LMA-60 (manufactured by Ajinomoto Co., Inc.);
N-[3-alkyl(12,14)oxy-2-hydroxypropyl]-arginine hydrochloride 60% aqueous solution
A*: The average value was +2.5 points or higher.

As is clear from the results in Table 12, when the blending quantity of the block-type alkylene oxide/ethylene oxide-dimer diol ether with a specific structure was in the range of 0.01 to 10 mass %, a roughly excellent hair conditioning effect was observed. From the standpoint of the texture in use such as smooth feeling, combing smoothness, and elastic feeling, it is especially preferable to blend 0.1 to 5 mass %.

Example 4

Blending into Bath Preparation Composition

Subsequently, the present inventors produced bath preparation composition, by a conventional method, of the respective examples and comparative examples with the blending compositions listed in Table 13 and Table 14, with the use of the above-described compounds 1 to 5 and comparative compounds 1 to 6. The evaluation tests were conducted for the below-described evaluations (1) to (6).
<Evaluation Method>
To a bathtub, 200 L of hot water (40° C.) was placed, 80 g of the bath preparation composition was added, and they were lightly stirred. Five minutes after that, 10 usability evaluation monitors were allowed to bathe for 10 minutes, and they were asked to evaluate the below-described items.
"Evaluation (1): Post-Bath Silky-Smooth Feeling of the Skin"
◎: Among 10 monitors, 8 or more monitors answered that the skin was silky-smooth after taking a bath.
○: Among 10 monitors, 5 or more and less than 8 monitors answered that the skin was silky-smooth after taking a bath.
Δ: Among 10 monitors, 3 or more and less than 5 monitors answered that the skin was silky-smooth after taking a bath.
X: Among 10 monitors, less than 3 monitors answered that the skin was silky-smooth after taking a bath.
"Evaluation (2): Post-Bath Free-of-Dryness of the Skin"
◎: Among 10 monitors, 8 or more monitors answered that the skin surface was not dry after taking a bath.
○: Among 10 monitors, 5 or more and less than 8 monitors answered that the skin surface was not dry after taking a bath.
Δ: Among 10 monitors, 3 or more and less than 5 monitors answered that the skin surface was not dry after taking a bath.
X: Among 10 monitors, less than 3 monitors answered that the skin surface was not dry after taking a bath.
"Evaluation (3): Post-Bath Free-of-Stickiness of the Skin"
◎: Among 10 monitors, 8 or more monitors answered that the stickiness of the skin was not present after taking a bath.
○: Among 10 monitors, 5 or more and less than 8 monitors answered that the stickiness of the skin was not present after taking a bath.
Δ: Among 10 monitors, 3 or more and less than 5 monitors answered that the stickiness of the skin was not present after taking a bath.
X: Among 10 monitors, less than 3 monitors answered that the stickiness of the skin was not present after taking a bath.
"Evaluation (4): Post-bath light fresh feeling of the skin"
◎: Among 10 monitors, 8 or more monitors answered that the skin was light fresh after taking a bath.
○: Among 10 monitors, 5 or more and less than 8 monitors answered that the skin was light fresh after taking a bath.
Δ: Among 10 monitors, 3 or more and less than 5 monitors answered that the skin was light fresh after taking a bath.
X: Among 10 monitors, less than 3 monitors answered that the skin was light fresh after taking a bath.
"Evaluation (5): Post-Bath Skin Itch Improving Effect"
◎: Among 10 monitors, 8 or more monitors answered that the skin itch was improved taking a bath.
○: Among 10 monitors, 5 or more and less than 8 monitors answered that the skin itch was improved after taking a bath.
Δ: Among 10 monitors, 3 or more and less than 5 monitors answered that the skin itch was improved after taking a bath.
X: Among 10 monitors, less than 3 monitors answered that the skin itch was improved after taking a bath.
"Evaluation (6): Moisturizing Effect 30 Minutes after Bathing"
◎: Among 10 monitors, 8 or more monitors answered that the moisturizing effect was present.
○: Among 10 monitors, 5 or more and less than 8 monitors answered that the moisturizing effect was present.
Δ: Among 10 monitors, 3 or more and less than 5 monitors answered that the moisturizing effect was present.
X: Among 10 monitors, less than 3 monitors answered that the moisturizing effect was present.

TABLE 13

|  | Ex. 4-1 | Ex. 4-2 | Ex. 4-3 | Ex. 4-4 | Ex. 4-5 |
|---|---|---|---|---|---|
| Propylene glycol | 45 | 45 | 45 | 45 | 45 |
| 1,3-butylene glycol | 40 | 40 | 40 | 40 | 40 |
| Sodium pyrrolidone carboxylate solution | 3 | 3 | 3 | 3 | 3 |
| Compound 1 | 10 | — | — | — | — |
| Compound 2 | — | 10 | — | — | — |
| Compound 3 | — | — | 10 | — | — |
| Compound 4 | — | — | — | 10 | — |
| Compound 5 | — | — | — | — | 10 |
| Anti-oxidant | proper quantity | proper quantity | proper quantity | proper quantity | proper quantity |
| Coloring material | proper quantity | proper quantity | proper quantity | proper quantity | proper quantity |
| Perfume | remainder | remainder | remainder | remainder | remainder |
| Evaluation(1) Post-bath silky-smooth feeling of the skin | ◎ | ◎ | ◎ | ◎ | ◎ |
| Evaluation(2) Post-bath free-of-dryness of the skin | ◎ | ◎ | ◎ | ◎ | ◎ |
| Evaluation(3) Post-bath free-of-stickiness of the skin | ◎ | ◎ | ◎ | ◎ | ◎ |
| Evaluation(4) Post-bath light fresh feeling of the skin | ◎ | ◎ | ◎ | ◎ | ◎ |
| Evaluation(5) Post-bath skin itch improving effect | ◎ | ◎ | ◎ | ◎ | ◎ |
| Evaluation(6) Moisturizing effect 30 minutes after bathing | ◎ | ◎ | ◎ | ◎ | ◎ |

TABLE 14

|  | Com. Ex. 4-1 | Com. Ex. 4-2 | Com. Ex. 4-3 | Com. Ex. 4-4 | Com. Ex. 4-5 | Com. Ex. 4-6 |
|---|---|---|---|---|---|---|
| Propylene glycol | 45 | 45 | 45 | 45 | 45 | 45 |
| 1,3-butylene glycol | 40 | 40 | 40 | 40 | 40 | 40 |
| Sodium pyrrolidone carboxylate solution | 3 | 3 | 3 | 3 | 3 | 3 |
| Comparative compound 1 | 10 | — | — | — | — | — |
| Comparative compound 2 | — | 10 | — | — | — | — |
| Comparative compound 3 | — | — | 10 | — | — | — |
| Comparative compound 4 | — | — | — | 10 | — | — |
| Comparative compound 5 | — | — | — | — | 10 | — |
| Comparative compound 6 | — | — | — | — | — | 10 |
| Anti-oxidant | proper quantity | proper quantity | proper quantity | proper quantity | proper quantity | proper quantity |
| Coloring material | proper quantity | proper quantity | proper quantity | proper quantity | proper quantity | proper quantity |
| Perfume | remainder | remainder | remainder | remainder | remainder | remainder |
| Evaluation(1) Post-bath silky-smooth feeling of the skin | X | X | ○ | ○ | X | X |
| Evaluation(2) Post-bath free-of-dryness of the skin | X | X | ○ | ○ | ○ | ○ |
| Evaluation(3) Post-bath free-of-stickiness of the skin | Δ | X | X | ◎ | ○ | ○ |
| Evaluation(4) Post-bath light fresh feeling of the skin | Δ | X | X | ◎ | ○ | ○ |
| Evaluation(5) Post-bath skin itch improving effect | X | X | Δ | ◎ | X | X |
| Evaluation(6) Moisturizing effect 30 minutes after bathing | ○ | Δ | Δ | Δ | ◎ | ○ |

As shown in Table 13, in the bath preparation compositions of Examples 4-1 to 4-5, wherein a block-type alkylene oxide/ethylene oxide-dimer diol ether with a specific structure (compounds 1 to 5) was blended, they were excellent in all the evaluations (1) to (6).

On the other hand, as shown in Table 14, in Comparative Example 4-1, wherein an alkylene oxide derivative with only oxyethylene portions (comparative compound 1) was blended, the post-bath silky-smooth feeling of the skin, post-bath free-of-dryness of the skin, post-bath free-of-stickiness of the skin, post-bath light fresh feeling of the skin, post-bath skin itch improving effect, etc. were poor. In Comparative Example 4-2, wherein an alkylene oxide derivative with only oxybutylene portions (comparative compound 2) was blended, the water solubility was poor when it was added to a bathtub, and it was poor in all evaluation items (1) to (6).

In Comparative Example 4-3, wherein a compound having a hydrogen atom at the terminal of the alkylene oxide derivative (comparative compound 3) was blended, the post-bath free-of-stickiness of the skin, post-bath light fresh feeling of the skin, post-bath skin itch improving effect, post-bath moisturizing effect were not satisfactory. In Comparative Example 4-4, wherein a compound with the terminal substituent having 6 carbon atoms (comparative compound 4) was used, the moisturizing effect 30 minutes after bathing was not satisfactory. In Comparative Example 4-5, wherein a random-type alkylene oxide derivative (comparative compound 5) was blended, the post-bath silky-smooth feeling of the skin and post-bath skin itch improving effect were not satisfactory. In Comparative Example 4-6, wherein an alkylene oxide/ethylene oxide derivative without the dimer diol section (comparative compound 6) was used, the post-bath silky-smooth feeling of the skin and post-bath skin itch improving effect were not satisfactory as was the case in Comparative Example 4-5.

Subsequently, the present inventors investigated in detail the preferable blending quantity of the above-described alkylene oxide derivative with a specific structure into a bath preparation composition. The results are shown in Table 15.

TABLE 15

|  | Ex. 4-6 | Ex. 4-7 | Ex. 4-8 | Ex. 4-9 |
|---|---|---|---|---|
| Compound 1 | 0.01 | 5 | 60 | 80 |
| Propylene glycol | 45 | 45 | 15 | 7 |
| 1,3-butylene glycol | 40 | 40 | 10 | 5 |
| Sodium pyrrolidone carboxylate solution | 3 | 3 | 3 | 3 |
| Anti-oxidant | proper quantity | proper quantity | proper quantity | proper quantity |
| Coloring material | proper quantity | proper quantity | proper quantity | proper quantity |
| Perfume | remainder | remainder | remainder | remainder |
| Evaluation (1) Post-bath silky-smooth feeling of the skin | ○ | ◎ | ◎ | ○ |
| Evaluation (2) Post-bath free-of-dryness of the skin | ○ | ◎ | ◎ | ◎ |
| Evaluation (3) Post-bath free-of-stickiness of the skin | ○ | ◎ | ◎ | Δ |
| Evaluation (4) Post-bath light fresh feeling of the skin | ○ | ◎ | ◎ | ○ |
| Evaluation (5) Post-bath skin itch improving effect | ○ | ◎ | ◎ | ◎ |
| Evaluation (6) Moisturizing effect 30 minutes after bathing | ○ | ◎ | ◎ | ◎ |

As shown in Table 15, the addition effect of the alkylene oxide derivative was recognized from about 0.1 mass %. However, it was particularly prominent at 5.0 mass % or higher. If the blending quantity was 80 mass % or higher, a slight stickiness was generated and it became difficult to sense a light fresh feeling. Thus, the blending up to about 60 mass % is preferable.

As is clear from the above results, when the block-type alkylene oxide derivative with a specific structure is blended in a bath preparation, a bath preparation composition having a post-bath itch improving effect and moisturizing effect and being free-of-dryness of the skin and excellent in light fresh feeling can be obtained.

In addition, the alkylene oxide derivative with the above-described specific structure also functions as a surfactant. Thus, it is possible to use it as a base agent excellent in stability.

Example 5

In the following, formulation examples blending the alkylene oxide derivative of the present invention are listed; however, the technical scope of the present invention is not limited by these. The obtained skin external preparations had a rough skin improving effect, and were safe and excellent in texture in use. In addition, the stability of a base agent was improved.

Formulation Example 1

Milky Lotion

| Phase A | |
|---|---|
| Squalane | 4.0 mass % |
| Oleylolate | 2.5 |
| Petrolatum | 1.5 |
| POB(18)POE(50) dimethyl dimer diol ether (dimer diol having 36 carbon atoms) | 2.0 |
| Evening primrose oil | 0.2 |
| Perfume | 0.1 |
| Antiseptic agent | proper quantity |
| Phase B | |
| 1,3-butylene glycol | 1.5 |
| Ethanol | 2.0 |
| Carboxyvinylpolymer | 0.2 |

-continued

| Potassium hydroxide | 0.1 |
|---|---|
| L-Arginine L-aspartate | 0.01 |
| Edetic acid | 0.05 |
| Purified water | remainder |

(Process)

Phase A and phase B were dissolved, respectively, by heating to 70° C. Phase A was added to phase B, and the emulsification was carried out with an emulsifying machine. The milky lotion was obtained by cooling the emulsion with a heat exchanger.

Formulation Example 2

Cream

| Phase A | |
|---|---|
| Stearic acid | 10.0 mass % |
| Stearyl alcohol | 3.5 |
| Butyl stearate | 6.0 |
| POB(12)POE(50) dimethyl dimer diol ether (dimer diol having 36 carbon atoms) | 1.5 |
| Monoglycerine ester stearate | 2.5 |
| Vitamin E acetate | 0.5 |
| Vitamin A palmitate | 0.1 |
| *Macadamia* oil | 0.5 |
| Perfume | 0.15 |
| Antiseptic agent | proper quantity |
| Phase B | |
| Glycerin | 6.0 |
| 1,2-Pentanediol | 2.0 |
| Sodium hyaluronate | 1.5 |
| Potassium hydroxide | 2.0 |
| Magnesium ascorbyl phosphate | 0.1 |
| L-Arginine hydrochloride | 0.01 |
| Trisodium edetate | 0.05 |
| Purified water | remainder |

(Process)

Phase A and phase B were dissolved, respectively, by heating to 70° C. Phase A was added to phase B, and the emulsification was carried out with an emulsifying machine. The cream was obtained by cooling the emulsion with a heat exchanger.

Formulation Example 3

Skin Lotion

| Phase A | |
| --- | --- |
| Ethanol | 5.0 mass % |
| POB(18)POE(61) dimethyl dimer diol ether (dimer diol having 36 carbon atoms) | 0.2 |
| 2-Ethylhexyl-P-dimethylaminobenzoate | 0.1 |
| Antiseptic agent | proper quantity |
| Perfume | 0.1 |
| Phase B | |
| Sodium DL-pyrrolidonecarboxylate | 0.3 |
| Nicotinamide | 0.2 |
| Dimorpholino pyridazinone | 0.1 |
| *Aloe* extract | 0.2 |
| Purified water | remainder |

(Process)

Phase A and phase B were dissolved, respectively. Phase A was added and solubilized to phase B, and the skin lotion was obtained.

Formulation Example 4

Foundation

| Phase A | |
| --- | --- |
| Cetanol | 3.5 mass % |
| Deodorized lanolin | 4.0 |
| Jojoba oil | 5.0 |
| Petrolatum | 2.0 |
| Squalane | 6.0 |
| Monoglycerine ester stearate | 2.5 |
| POB(25)POE(52) dimethyl dimer diol ether (dimer diol having 36 carbon atoms) | 1.5 |
| Pyridoxine tripalmitate | 0.1 |
| Antiseptic agent | proper quantity |
| Perfume | 0.3 |
| Phase B | |
| Propylene glycol | 10.0 |
| Blending powder | 12.0 |
| Trisodium edetate | 0.5 |
| Purified water | remainder |

(Process)

Phase A and phase B were dissolved, respectively, by heating to 70° C. Phase A was added to phase B, and the emulsification was carried out with an emulsifying machine. The foundation was obtained by cooling the emulsion with a heat exchanger.

Formulation Example 5

Lotion Mask

| Phase A | |
| --- | --- |
| Ethanol | 8.0 mass % |
| POE(52)POP(30) dimethyl dimer diol ether (dimer diol having 36 carbon atoms) | 0.5 |
| Menthyl lactate | 0.002 |
| Antiseptic agent | proper quantity |
| Perfume | 0.01 |
| Phase B | |
| Birch extract | 0.2 |
| Caustic potash | proper quantity |
| Purified water | remainder |

(Process)

A lotion was prepared by adding phase A to phase B, and the lotion mask was obtained by further impregnating the lotion into a nonwoven cloth.

Formulation Example 6

Makeup Cleansing Gel

| | | |
| --- | --- | --- |
| (1) | Hydroxyethylcellulose | 0.1 mass % |
| (2) | Carboxyvinylpolymer | 0.4 |
| (3) | Acrylic acid/alkyl methacrylate copolymer | 0.2 |
| (4) | Trisodium edetate | proper quantity |
| (5) | Sodium methyl cocoyl taurate | 0.1 |
| (6) | Monoisostearic acid polyethyleneglycol | 0.5 |
| (7) | POB(18)POE(50) dimethyl dimer diol ether (dimer diol having 36 carbon atoms) | 5.0 |
| (8) | Glycerin | 5.0 |
| (9) | Potassium hydroxide | proper quantity |
| (10) | Alcohol | 5.0 |
| (11) | Antiseptic agent | proper quantity |
| (12) | Decamethylcyclopentasiloxane | 18.0 |
| (13) | Methylpolysiloxane | 3.0 |
| (14) | Perfume | proper quantity |
| (15) | Purified water | remainder |

(Process and Evaluation)

Components (1) to (9) were added to component (15) and dissolved by stirring to obtain the water phase. Then, the solution in which component (11) was dissolved in component (10) was added to the water phase. Components (12) to (14) were further added, and the emulsification was carried out with an emulsifying machine to obtain a makeup cleansing gel. When the obtained makeup cleansing gel was directly applied to cosmetics and rinsed with water, the cleansing gel was good in texture in use, especially excellent in rinsability during cleansing, light fresh feeling after cleansing, and the absence of frictional feeling. In addition, the cosmetic cleansing effect was high and the skin irritation was also low.

Formulation Example 7

Makeup Cleansing Gel

| | |
|---|---|
| (1) Hydroxyethylcellulose | 0.05 mass % |
| (2) Carboxyvinylpolymer | 0.45 |
| (3) Acrylic acid/alkyl methacrylate copolymer | 0.1 |
| (4) Trisodium edetate | proper quantity |
| (5) Sodium methyl cocoyl taurate | 0.01 |
| (6) POB(18)POE(41) dimethyl dimer diol ether (dimer diol having 36 carbon atoms) | 7.0 |
| (7) Glycerin | 2.0 |
| (8) Propylene glycol | 3.0 |
| (9) Sodium polyaspartate solution | proper quantity |
| (10) Chamomilla extract | proper quantity |
| (11) Potassium hydroxide | proper quantity |
| (12) Alcohol | 5.0 |
| (13) Polyoxyethylene hydrogenated castor oil | 0.1 |
| (14) Antiseptic agent | proper quantity |
| (15) Decamethylcyclopentasiloxane | 18.0 |
| (16) Methylpolysiloxane | 3.0 |
| (17) Perfume | proper quantity |
| (18) Purified water | remainder |

(Process and Evaluation)

Components (1) to (11) were added to component (18) and dissolved by stirring to obtain the water phase. Then, the solution in which component (13) to (14) was dissolved in component (12) was added to the water phase. Components (15) to (17) were further added, and the emulsification was carried out with an emulsifying machine to obtain a makeup cleansing gel. When the obtained makeup cleansing gel was directly applied to cosmetics and rinsed with water, the cleansing gel was good in texture in use, especially excellent in rinsability during cleansing, light fresh feeling after cleansing, and the absence of frictional feeling. In addition, the cosmetic cleansing effect was high and the skin irritation was also low.

Formulation Example 8

Cleansing Lotion

| | |
|---|---|
| (1) Ethanol | 35.0 mass % |
| (2) Alkyl glucoside | 1.0 |
| (3) Polyethyleneglycol | 5.0 |
| (4) Glycerin | 3.0 |
| (5) POB(04)POE(13) dimethyl dimer diol ether (dimer diol having 36 carbon atoms) | 1.0 |
| (6) Antiseptic agent | proper quantity |
| (7) Purified water | remainder |

(Process and Evaluation)

Component (6) was dissolved in component (1) and added to component (7), components (2) to (5) were further added to it, and they were dissolved by stirring to obtain a cleansing lotion. The obtained cleansing lotion was applied on cotton, and makeup stains on the face were removed. The cleansing lotion was good in texture in use, especially excellent in rinsability during cleansing, light fresh feeling after cleansing, and the absence of frictional feeling. In addition, the cosmetic cleansing effect was high and the skin irritation was also low.

Formulation Example 9

Cleansing Cream

| | |
|---|---|
| (1) Cetanol | 2.0 mass % |
| (2) Beeswax | 2.0 |
| (3) Stearic acid | 3.0 |
| (4) Petrolatum | 8.0 |
| (5) Squalane | 37.0 |
| (6) Isopropyl myristate | 10.0 |
| (7) POB(32)POE(35) dimethyl dimer diol ether (dimer diol having 36 carbon atoms) | 2.5 |
| (8) Glyceryl monostearate | 2.5 |
| (9) Antiseptic agent | proper quantity |
| (10) Perfume | proper quantity |
| (11) Glycerin | 2.0 |
| (12) Propylene glycol | 5.0 |
| (13) Potassium hydroxide | 0.1 |
| (14) Purified water | remainder |

(Process and Evaluation)

Components (1) to (4) and components (6) to (10) were added to component (5) and dissolved with stirring to give the oil phase. Components (11) to (13) were dissolved in component (14) to give the water phase. They were respectively heated to 70° C. and dissolved, then the former (oil phase) was added to the latter (water phase). This was emulsified with an emulsifying machine and cooled to 30° C. with a heat exchanger. This was filled in a container and a cleansing cream was obtained. The obtained cleansing cream was applied on the facial surface and makeup stains were removed. The cleansing cream was good in texture in use, in particular, excellent in the rinsability during cleansing, light fresh feeling after cleansing, and the absence of frictional feeling. In addition, the cosmetic cleansing effect was high and the skin irritation was low.

Formulation Example 10

Body Shampoo

| | |
|---|---|
| (1) Hydroxypropylmethylcellulose | 0.1 mass % |
| (2) Glycerin | 10.0 |
| (3) Dipropyleneglycol | 5.0 |
| (4) Triethanolamine laurate | 12.0 |
| (5) Betaine lauryl dimethyl aminoacetate | 5.0 |
| (6) Coconut oil fatty acid diethanolamide | 3.0 |
| (7) POB(17)POE(30) dimethyl dimer diol ether (dimer diol having 36 carbon atoms) | 5.0 |
| (8) Chamomilla extract | proper quantity |
| (9) Trisodium edetate | proper quantity |
| (10) Antiseptic agent | proper quantity |
| (11) Coloring agent | proper quantity |
| (12) Perfume | proper quantity |
| (13) Purified water | remainder |

(Process and Evaluation)

Component (1) was added to component (13) and dispersed with stirring. The dispersion was heated to 70° C., and components (2) to (12) were added and dissolved with stirring. Then, a body shampoo was obtained by cooling with a heat exchanger. When the obtained body shampoo was foamed with water, applied, and rinsed with water, the body shampoo was good in texture in use, in particular, excellent in the rinsability during cleansing, light fresh feeling after cleansing, and the absence of frictional feeling. In addition, the cosmetic cleansing effect was high and the skin irritation was low.

Formulation Example 11

Milled Soap

| | | |
|---|---|---|
| (1) Sodium soap | | remainder |
| (2) Potassium soap | | 5.0 mass % |
| (3) Sodium chloride | | 0.3 |
| (4) Glycerin | | 0.5 |
| (5) Lauric acid | | 5.0 |
| (6) POB(40)POE(50) dimethyl dimer diol ether (dimer diol having 36 carbon atoms) | | 3.0 |
| (7) Coloring agent | | proper quantity |
| (8) Trisodium edetate | | proper quantity |
| (9) Perfume | | proper quantity |

(Process and Evaluation)

Components (1) to (9) were mixed with heating at 60° C., and the solution was poured into a mold, cooled, and solidified to obtain a milled soap. When the obtained soap was foamed with water, applied, and rinsed with water, the soap was good in texture in use, in particular, excellent in the rinsability during cleansing, light fresh feeling after cleansing, and the absence of frictional feeling. In addition, the cosmetic cleansing effect was high and the skin irritation was low.

Formulation Example 12

Hair Rinse

| | |
|---|---|
| Cetyltrimethylammonium chloride | 0.6 mass % |
| Cetostearyl alcohols (C16/C18 = 6/4) | 4.0 |
| Dimethyl polysiloxane (5 cs) | 3.0 |
| Glyceryl monostearate | 1.0 |
| Liquid paraffin | 3.0 |
| POB(25)POE(52) dimethyl dimer diol ether (carbon number 36 dimer diol) | 8.0 |
| Glyceryl monostearate | 1.0 |
| Glycerin | 5.0 |
| Propylene glycol | proper quantity |
| Pigment | proper quantity |
| Perfume | proper quantity |
| Purified water | remainder |

(Evaluation)

This hair rinse was excellent in the texture in the use for hair, in particular, was excellent in the light rustling feeling, moist feeling, smooth feeling, supple feeling, and elastic feeling.

Formulation Example 13

Hair Treatment Cream

| | |
|---|---|
| Behenyltrimethylammonium chloride | 3.0 mass % |
| Cetostearyl alcohols (C16/C18 = 6/4) | 6.5 |
| Behenyl alcohol | 2.0 |
| Dimethyl polysiloxane (20 cs) | 3.0 |
| 2-octyldodecanol | 2.0 |
| Polyoxyethylene hydrogenated castor oil derivative (ethylene oxide 60 mol adduct) | 0.3 |
| Polyoxyethylene stearyl ether (ethylene oxide 4 mol adduct) | 1.0 |
| Soybean lecithin | 0.5 |
| Liquid paraffin | 3.0 |
| POB(32)POE(35) dimethyl dimer diol ether (dimer diol having 36 carbon atoms) | 5.0 |
| Glycerin | 10.0 |
| Dipropylene glycol | 5.0 |
| Antiseptic agent | proper quantity |
| Pigment | proper quantity |
| Perfume | proper quantity |
| Purified water | remainder |

(Evaluation)

This hair treatment cream was excellent in the texture in the use for hair, in particular, was excellent in the light rustling feeling, moist feeling, smooth feeling, supple feeling, and elastic feeling.

Formulation Example 14

Hair Rinse

| | |
|---|---|
| Stearic acid diethylaminoethylamide | 0.6 mass % |
| Cetyl alcohol | 2.0 |
| Stearyl alcohol | 1.0 |
| Dimethyl polysiloxane (5 cs) | 3.0 |
| Glycerol monostearate | 1.0 |
| Liquid paraffin | 3.0 |
| POB(4)POE(13) dimethyl dimer diol ether (dimer diol having 36 carbon atoms) | 8.0 |
| Glycerol monostearate | 1.0 |
| Glycerin | 5.0 |
| Propylene glycol | 5.0 |
| L-glutamic acid | 0.6 |
| Antiseptic agent | proper quantity |
| Pigment | proper quantity |
| Perfume | proper quantity |
| Purified water | remainder |

(Evaluation)

This hair rinse was excellent in the texture in the use for hair, in particular, was excellent in the light rustling feeling, moist feeling, smooth feeling, supple feeling, and elastic feeling.

Formulation Example 15

Hair Treatment Cream

| | |
|---|---|
| Stearic acid dimethylaminopropylamide | 3.0 mass % |
| Cetyl alcohol | 6.5 |
| Behenyl alcohol | 2.0 |
| Stearic acid | 2.0 |
| Dimethyl polysiloxane (20 cs) | 3.0 |
| 2-octyldodecanol | 2.0 |
| Polyoxyethylene hydrogenated castor oil derivative (ethylene oxide 60 mol adduct) | 0.3 |
| Polyoxyethylene stearyl ether (ethylene oxide 4 mol adduct) | 1.0 |
| Liquid paraffin | 3.0 |
| POB(15)POE(45) dimethyl dimer diol ether (dimer diol having 36 carbon atoms) | 5.0 |
| Glycerin | 10.0 |
| Dipropylene glycol | 5.0 |
| L-glutamic acid | 1.0 |
| Antiseptic agent | proper quantity |
| Pigment | proper quantity |

-continued

| | |
|---|---|
| Perfume | proper quantity |
| Purified water | remainder |

(Evaluation)

This hair treatment cream was excellent in the texture in the use for hair, in particular, was excellent in the light rustling feeling, moist feeling, smooth feeling, supple feeling, and elastic feeling.

Formulation Example 16

Liquid Bath Preparation

| (Blending components) | (mass %) |
|---|---|
| Propylene glycol | 10.0 |
| 1,3-butylene glycol | 12.0 |
| Liquid paraffin | 35.0 |
| Cetyl octanoate | 5.0 |
| Squalene | 5.0 |
| Polyoxyethylene(15) oleyl ether | 8.0 |
| POB(25)POE(52) dimethyl dimer diol ether (dimer diol having 36 carbon atoms) | 20.0 |
| Antioxidant | proper quantity |
| Coloring agent | proper quantity |
| Perfume | proper quantity |

(Process and Evaluation)

At an ordinary temperature, cetyl octanoate, and squalene were added to liquid paraffin and stirred. Then, propylene glycol, 1,3-butylene glycol, POB(25)POE(52) dimethyl dimer diol ether, antioxidant, coloring agent, and perfume were added to polyoxyethylene(15) oleyl ether and stirred. These were mixed with stirring; thus the desired bath preparation was obtained. The obtained bath preparation was a post-bath skin itch improving effect, moisturizing effect, and free-of-dryness of the skin, and the light fresh feeling was excellent.

Formulation Example 17

Powder Bath Preparation

| (Blending components) | (mass %) |
|---|---|
| Sodium sulfate | 50.0 |
| Sodium hydrogen carbonate | 20.0 |
| Sodium sesquicarbonate | 5.0 |
| Borax | 5.0 |
| Sodium chloride | 10.0 |
| POB(12)POE(50) dimethyl dimer diol ether (dimer diol having 36 carbon atoms) | 3.0 |
| Melilot extract | 1.0 |
| Coloring agent | proper quantity |
| Perfume | proper quantity |

(Process and Evaluation)

At an ordinary temperature, sodium sulfate, sodium hydrogencarbonate, sodium sesquicarbonate, borax, sodium chloride, and a coloring agent were stirred. Then, POB (12) POE (50) dimethyl dimer diol ether, melilot extract, and perfume were added and mixed with stirring; thus the desired bath preparation was obtained. The obtained bath preparation did not generate post-bath skin stickiness, there was a moist feeling, smooth feeling, and a heat retention effect, and the moisturizing effect was excellent.

What is claimed is:

1. An alkylene oxide derivative represented by the below-described general formula (I):

$$Z\text{—}\{O\text{-}[(AO)_a\text{-}(EO)_b]\text{-}R\}_2 \quad (I)$$

wherein, Z is the residue obtained by removing hydroxyl groups from the dimer diol; EO is an oxyethylene group; AO is an oxyalkylene group having 3 to 4 carbon atoms; the addition form is block-type; the symbols a and b are respectively the average addition mole numbers of the above-described oxyalkylene group and the oxyethylene group and they are $1 \leq a \leq 150$ and $1 \leq b \leq 150$; the percentage of the oxyethylene groups with respect to the sum of the oxyalkylene groups having 3 to 4 carbon atoms and the oxyethylene groups is 10 to 99 mass %; and Rs may be either identical to or different from each other and they are hydrocarbon groups having 1 to 4 carbon atoms.

2. An alkylene oxide derivative according to claim 1, wherein AO shown in the general formula (I) is an oxybutylene group.

3. An alkylene oxide derivative according to claim 1, wherein Z shown in the general formula (I) is a dimer diol residue having 24 to 48 carbon atoms.

4. A skin external preparation comprising the alkylene oxide derivative according to claim 1.

5. A skin external preparation according to claim 4, wherein the content of the above-described alkylene oxide derivative is 0.01 to 70 mass %.

6. A rough skin improving agent comprising the alkylene oxide derivative according to claim 1 as the active component.

7. A usability-improving agent for cosmetics comprising the alkylene oxide derivative according to claim 1 as the active component.

8. An alkylene oxide derivative according to claim 2, wherein Z shown in the general formula (I) is a dimer diol residue having 24 to 48 carbon atoms.

9. A skin external preparation comprising the alkylene oxide derivative according to claim 2.

10. A skin external preparation comprising the alkylene oxide derivative according to claim 3.

11. A rough skin improving agent comprising the alkylene oxide derivative according to claim 2 as the active component.

12. A rough skin improving agent comprising the alkylene oxide derivative according to claim 3 as the active component.

13. A usability-improving agent for cosmetics comprising the alkylene oxide derivative according to claim 2 as the active component.

14. A usability-improving agent for cosmetics comprising the alkylene oxide derivative according to claim 3 as the active component.

* * * * *